United States Patent [19]

Mehra

[11] Patent Number: 4,511,381

[45] Date of Patent: * Apr. 16, 1985

[54] PROCESS FOR EXTRACTING NATURAL GAS LIQUIDS FROM NATURAL GAS STREAMS WITH PHYSICAL SOLVENTS

[75] Inventor: Yuv R. Mehra, Odessa, Tex.

[73] Assignee: El Paso Hydrocarbons Company, Odessa, Tex.

[*] Notice: The portion of the term of this patent subsequent to Dec. 20, 2000 has been disclaimed.

[21] Appl. No.: 507,564

[22] Filed: Jun. 24, 1983

Related U.S. Application Data

[63] Continuation-in-part of Ser. No. 374,270, May 3, 1982, Pat. No. 4,421,534.

[51] Int. Cl.³ .............................................. F25J 3/02
[52] U.S. Cl. .......................................... 62/17; 55/73; 55/76
[58] Field of Search ................. 62/17, 20, 23, 9, 11; 55/68, 73, 76

[56] References Cited

U.S. PATENT DOCUMENTS

| | | | |
|---|---|---|---|
| 2,139,375 | 12/1938 | Mills et al. | 23/2 |
| 2,290,957 | 7/1942 | Hachmuth | 196/8 |
| 2,649,166 | 8/1953 | Porter et al. | 183/115 |
| 2,849,371 | 8/1958 | Gilmore | 196/2 |
| 3,287,262 | 11/1966 | Jones | 208/341 |
| 3,362,133 | 1/1968 | Kutsher et al. | 55/44 |
| 3,594,985 | 7/1971 | Ameen et al. | 55/73 |
| 3,664,091 | 5/1972 | Hegwer | 55/29 |
| 3,737,392 | 6/1973 | Ameen et al. | 252/364 |
| 3,831,346 | 8/1974 | Sharp et al. | 568/621 |
| 3,837,143 | 9/1974 | Sutherland et al. | 55/32 |
| 3,877,893 | 4/1975 | Sweny et al. | 55/32 |
| 4,252,548 | 2/1981 | Markbreiter et al. | 62/17 |
| 4,276,057 | 6/1981 | Becker et al. | 50/40 |
| 4,302,220 | 11/1981 | Volkamer et al. | 55/32 |
| 4,318,715 | 3/1982 | Chou | 55/44 |
| 4,345,918 | 8/1982 | Meissner | 55/38 |
| 4,421,535 | 12/1983 | Mehra | 62/17 |

OTHER PUBLICATIONS

Sweny, John W., "High $CO_2$–High $H_2S$ Removal with Selexol Solvent," Mar. 17–19, 1980, 59th Annual GPA Convention, Houston, Texas.

Primary Examiner—Frank Sever
Attorney, Agent, or Firm—Depaoli & O'Brien

[57] ABSTRACT

A continuous process for selective countercurrent extraction of $C_{2+}$ hydrocarbons from a natural gas stream with a physical solvent while at pipeline pressures to produce a residue natural gas stream meeting pipeline specifications and a liquid hydrocarbon product having a composition which can be readily adjusted to any selected degree in accordance with market conditions so that profitability of the extraction operation can be maximized at all times. The rich solvent is let down in pressure through successive flashing stages to produce a liquid product, and the stripped solvent is recirculated to the extraction step. The versatility of the process is achieved by using the following steps, in order of importance: (1) selectively varying the flow rate of the solvent with respect to the flow rate of the natural gas stream; (2) selectively varying the flashing pressure for one or more successive flashing stages; (3) recycling the flashed $C_{1+}$ undesirable gases to the extraction step; and (4) rejecting selected components of the liquid product in a stripping column for the liquid hydrocarbon product by: (a) selectively varying the pressure in the column, and (b) selectively varying the temperature at the bottom of the column. The rejected components are also recycled to the extraction step and are $C_1$, $C_1+C_2$, $C_1+C_2+C_3$, or $C_1+C_2+C_3+C_4$. If water is present in significant quantities, the solvent is regenerated before recycling it to the extraction step.

36 Claims, 5 Drawing Figures

PROCESS FOR EXTRACTING NATURAL GAS LIQUIDS FROM NATURAL GAS STREAMS WITH PHYSICAL SOLVENTS

RELATED APPLICATION

This is a continuation-in-part of co-pending U.S. application Ser. No. 374,270, filed May 3, 1982, now U.S. Pat. No. 4,421,534, of Yuv R. Mehra, entitled "Process for Recovery of Natural Gas Liquids from a Sweetened Natural Gas Stream".

BACKGROUND OF THE INVENTION

1. Field of the Invention

This invention relates to the treatment of hydrocarbons and more specifically relates to separating and recovering ethane and higher boiling hydrocarbons from the methane in a natural gas stream which is sour or which has been sweetened by removal of acidic components, such as $CO_2$, $H_2S$, RSH, RSSR, and ammonia.

2. Review of the Prior Art

Raw natural gas as it originates from subterranean reservoirs, either out of solution from crude oil or unassociated with crude oil, can be classified as rich natural gas, rich gas, or lean natural gas. These terms are relative.

Rich natural gas contains a mixture of individual gaseous constituents, some of which can be liquified at atmospheric temperatures and pressures when isolated. The quantities of each component vary from one gas to another, with methane as a usual majority component. Other hydrocarbon components include ethane, propane, isobutane, normal butane, isopentane, normal pentane, hexane, heptane, octane. and nonane, in the order of increasing molecular weight and increasing boiling temperature. Usually, natural gases contain some gaseous contaminants such as nitrogen, carbon dioxide, carbonyl sulfide, hydrogen sulfide, mercaptans, disulfides, ammonia, and water. However, all of these impurities except water and nitrogen are removed by sweetening. Such a sweet natural gas stream is a subject of this invention.

"Lean natural gas" is a term applied to a natural gas which consists of only the lower molecular weight gaseous components, consisting for the most part of methane with variant quantities of ethane, propane, and only very small traces of higher molecular weight components, if any. Such a lean natural gas can occur naturally but generally results from processing a rich natural gas in accordance with recognized industrial methods.

A sweet natural gas stream contains nitrogen, methane, ethane, propane, iso and normal butanes, iso and normal pentanes, hexane, heavier hydrocarbon components, and water. However, there are no acid gases or other acidic impurities, such as $CO_2$, COS, $H_2S$, RSH, RSSR, and ammonia.

If a natural gas is mostly methane with minor concentrations of ethane, propane, and butanes, it is called a "dry gas", meaning that it has a very low hydrocarbon dew point. The larger the quantity of heavier hydrocarbons such as pentane and higher homologs, e.g., to $C_{18}$, the higher is the hydrocarbon dew point. Frequently, the heavier hydrocarbons are present in sufficient quantities to justify passing the gas through a "gasoline extraction plant" which removes ethane and propane in addition to the heavier hydrocarbons. In some instances, the hydrocarbon dew point is high enough to require a "dew point control station" which removes enough of the heavy hydrocarbons to lower the dew point sufficiently to permit pipeline transmissions but does not remove as much of the heavier materials, in addition to the large percentage of the propane and ethane, as is removed by a gasoline extraction plant. Furthermore, the gas coming from the wellhead is usually saturated with water which must be largely removed in order to prevent the formation of ice and hydrates or the accumulation of water which can block the flow and cause corrosion.

Numerous processes have been used to extract liquids from natural gas streams. These processes include oil absorption, refrigerated oil absorption, simple refrigeration, cascaded refrigeration, Joule-Thompson expansion, and cryogenic turbo-expansion.

Oil absorption processes, such as that described in U.S. Pat. No. 2,428,521, are the original separation processes and commonly recover butanes plus heavier components, with some amounts of propane, from natural gas streams; recoveries are typically: ethane 4%, propane 24%, butanes 75%, and gasoline ($C_5+$) 87%. Refrigerated oil absorption processes are similar to the oil absorption processes except that the oil is cooled by external refrigeration before absorption of liquid components from the gas streams. The recoveries of propane plus components are improved by cooling the absorption oil; recoveries are typically: ethane 15%, propane 65%, butane 90%, and gasoline 95%. Plants using these processes are extremely complex and energy extensive.

A simple refrigeration process includes cooling the gas directly with a single refrigerant, such as propane. Condensed liquids are separated from the gas and are pumped to product pipelines. The recoveries of a simple refrigeration system are better than those of oil absorption units and are typically: $C_2$ 35%, $C_3$ 80%, $C_4$'S 93%, and gasoline 97%. A cascaded refrigeration process includes several levels of refrigeration, using at least two refrigerants, such as ethane refrigerant cascaded into a propane refrigerant cycle. The recoveries of cascade refrigeration systems are quite good and are typically: $C_2$ 70%, $C_3$ 96%, $C_4$'S 99%, and gasoline 100%, but units using these processes are not very economical because of high operating and installing costs.

The Joule-Thompson process is a step forward because it uses the refrigeration from the components of a natural gas stream by letting down its pressure, typical recoveries being $C_2$ 75%, $C_3$ 96%, $C_4$'S 99%, and gasoline 100%. When the residue gas is required at essentially the same pressure as the inlet gas, however, this process becomes quite expensive. A cryogenic expander process has less energy consumption than a Joule-Thompson process for a given recovery, primarily because a portion of the total recompression of residue gas is provided by the turbo-expander; recoveries are typically: $C_2$ 85%, $C_3$ 97%, $C_4$'S 100%, and gasoline 100%. The Joule-Thompson and cryogenic expander processes are primarily used when ethane is to be extracted from natural gas streams. These processes can achieve ethane recoveries as high as 85% to 90%.

In summary, the oil absorption, refrigerated oil absorption, simple refrigeration, and cascaded refrigeration processes operate at the pipeline pressures, without letting down the gas pressure, but the recovery of desirable liquids (ethane plus heavier components) is quite poor, with the exception of the cascaded refrigeration process which has extremely high operating costs but achieves good ethane and propane recoveries. The Joule-Thompson and cryogenic expander processes achieve high ethane recoveries by letting down the pressure of the entire inlet gas, which is primarily methane (typically 80–85%), but recompression of most of the inlet gas is quite expensive.

In all of the above processes, the ethane plus heavier components are recovered in a specific configuration determined by their composition in the raw natural gas stream and equilibrium at the key operating conditions of pressure and temperature within the process.

Under poor economic conditions when ethane price as petrochemical feedstock is less than its equivalent fuel price and when the propane price for feedstock usage is attractive, the operator of a natural gas liquid extraction plant is limited as to operating choice because he is unable to minimize ethane recovery and maximize propane recovery in response to market conditions.

The refrigeration process which typically recovers 80% of the propane also typically requires the recovery of 35% of the ethane. In order to boost propane recovery to the 95+% level, cascaded refrigeration, Joule-Thompson, or cryogenic turbo expander processes would have to be used while simultaneously boosting the ethane recovery to 70+% at a considerably larger capital investment.

Extraction processes are available that employ liquids other than hydrocarbon oils for removal of acidic components, including $H_2S$ and $CO_2$, and water. These liquids comprise propylene carbonate, N-methyl pyrrolidone, glycerol triacetate, polyethyleneglycol dimethyl ether, triethylolamine, tributyl phosphate, and gamma butyrolactone.

U.S. Pat. No. 3,362,133 is directed to sour natural gas mixtures containing $H_2S$ and $CO_2$ and teaches the selection of any dialkyl ether of a polyalkylene glycol as the ether component of a solvent for withdrawing $H_2S$. A mixture of six dimethyl ethers of polyethylene glycol (DMPEG) is said to be effective. The solvent/gas ratio is 0.1 to 1.8 pounds of solvent per standard cubic foot (scf) of $H_2S$ to be absorbed, because less than this amount will not effectively remove $H_2S$ and larger amounts result in absorption of substantial quantities of $CO_2$. The $H_2S$-rich and $CO_2$-rich DMPEG solvent is flashed at 15–500 psi lower pressure than in the absorber (preferably, 65 psi lower pressure) within a flash tank which produces gas containing substantially all of the $CO_2$ and one-fourth of the $H_2S$. This gas is returned to the absorber. The DMPEG solvent is heated, reduced in pressure, and passed through a packed column as air is passed upwardly. The solvent must contain no more than 0.001% $H_2S$ when it returns to the absorber. The $CO_2$ and $H_2S$ vented from top of the stripping column contain dissolved hydrocarbons which represent a significant loss.

U.S. Pat. No. 3,770,622 relates to treatment of natural gas for removing three troublesome components: $CO_2$, $H_2S$, and hydrocarbons heavier than methane. The preferred solvent is propylene carbonate, but polyethylene glycol dimethyl ether may be used. The solvent is passed in counter-flowing contact with a natural gas mixture, to remove $CO_2$ and/or $H_2S$ acid gases plus $C_2$–$C_{18}$ hydrocarbon components from methane gas streams. $CO_2$, $H_2S$, and light hydrocarbons are partially separated from the solvent by flashing. Liquid hydrocarbons ($C_4$ and heavier) having gasoline value are then separated in a settler from liquid solvent and from a vapor-phase mixture of $C_2$–$C_{12}$ hydrocarbon vapor, $H_2S$, and/or $CO_2$. In the example, the three flash streams together contain 43.76% of $C_2$-$C_{12}$ hydrocarbons which represent a significant loss of desirable hydrocarbons with $CO_2$ and $H_2S$ vent gases.

U.S. Pat. No. 3,837,143 describes simultaneous dehydration and sweetening of natural gas to produce therefrom a purified natural gas having a low dew point and a low sulfur content by using a normally liquid dialkylether of a polyalkylene glycol containing 2–15% water by weight in direct contact with the natural gas. As described in this patent, the natural gas is significantly lean with respect to heavier hydrocarbons. Example 1 illustrates a loss of 74% of $C_2+$ hydrocarbons with the $CO_2$ and $H_2S$ vent stream while Example 2 shows a loss of 11.6% for $C_2+$ hydrocarbons. Therefore, this process exacts a significant economic penalty for sweetening wet natural gases with DMPEG.

U.S. Pat. No. 4,052,176 relates to a synthesis gas containing no $C_2+$ hydrocarbons and teaches further purification thereof with dimethyl ether of polyethylene glycol to absorb remaining $CO_2$, $H_2S$, and COS.

U.S. Pat. No. 4,070,165 teaches sweetening a raw natural gas before it is liquefied by countercurrent contact with a lean amine solution, dehydrating by contact with a dry glycol stream, and removal of heavier hydrocarbons (after depressurizing) by scrubbing with a lean hydrocarbon stream which is then fractionated to produce methane, ethane, and propane. Dimethyl ether of polyethylene glycol is mentioned as useful for both water and $H_2S$ removal. Natural gases, that are suitable for liquefaction and that exist at pressures higher than 800 psig, usually are lean, containing few $C_2+$ heavier hydrocarbons.

As presented at the 50th Annual Gas Processors Association Convention, Mar. 17–19, 1980, in a paper entitled "High $CO_2$—High $H_2S$ Removal with SELEXOL Solvent" by John W. Sweny, the relative solubility in DMPEG of $CO_2$ over methane is 15.0 while that of propane is 15.3. The relative solubility in DMPEG of $H_2S$ over methane is 134 versus 165 for hexane in DMPEG. The relative solubilities in DMPEG of iso and normal butanes and iso and normal pentanes are in between those of propane and $H_2S$. These data indicate that if $CO_2$ and $H_2S$ are present in a natural gas stream which contains $C_2+$ heavier hydrocarbons desirable for petrochemical industry feedstocks, substantial quantities of $C_2+$ hydrocarbons will be lost with $CO_2$ and $H_2S$ vent streams when treated with DMPEG.

Sweet natural gas is usually saturated with water at its ambient temperature which may have a range of 75°–120° F., so that its water content may vary from 20 pounds to more than 50 pounds per million standard cubic feet. However, difficulties are frequently met while pumping such natural gas unless the water content is reduced to a value of less than 12 pounds, preferably less than 7 pounds, of water per million standard cubic feet of natural gas. In terms of dew point, a natural gas having a dew point of 30° F., preferably 20° F. or lower, is generally considered safe for transportation in a pipeline. Dehydration can be carried out under a wide range of pressures from 15 to 5000 psig, but it is usually carried out at pipeline pressures of 500–1500 psig and generally near 1000 psig.

There is nevertheless a need for a process wherein ethane and heavier hydrocarbons and water can be simultaneously removed to a selected degree from methane contained in a natural gas stream without inclusion of steps specifically involving drying thereof. There is further a need for a process wherein propane and heavier hydrocarbons can be extracted to any selected degree from a natural gas without the need to extract significant quantities of ethane. There is still further a need for a process wherein butanes and heavier components can be recovered to any selected degree from a natural gas stream at extremely high recoveries without the need simultaneously to recover propane and ethane from the natural gas stream. There is at times also a need for a process wherein pentanes and heavier hydrocarbons can be recovered to any selected degree from a natural gas stream at extremely high recoveries without the need simultaneously to recover ethane, propane, and butanes therefrom. There is additionally a need for a process wherein any natural gas, from very sour to entirely sweet, can be handled by the same equipment while simultaneously dehydrating the gas and recovering the heavier hydrocarbons.

SUMMARY OF THE INVENTION

The object of this invention is to provide an extraction process for removing ethane plus heavier hydrocarbon components from a natural gas stream by contact with a hydrocarbon extraction solvent according to an extremely flexible wide range of ethane recoveries without requiring additional equipment therefor.

Another object is to provide a process for removing $C_3+$ components from a natural gas stream by contact with a hydrocarbon extraction solvent without requiring the recovery of ethane from such natural gas stream and while maintaining high recovery levels for $C_3+$ components.

A further object of this invention is to provide a process for removing $C_4+$ hydrocarbons from a natural gas stream by contact with a hydrocarbon extraction solvent without requiring the recovery of ethane and propane from such natural gas stream while achieving extremely high butane plus heavier hydrocarbon recoveries.

A still further object is to provide a process for removing $C_5+$ components from a natural gas stream by contact with a hydrocarbon extraction solvent without requiring the recovery of ethane, propane, or butanes from such natural gas stream while achieving extremely high pentanes plus heavier hydrocarbon recoveries.

An additional object is to provide a process for removing $C_2+$ components, water, and acid components from a sour natural gas stream by contact with a hydrocarbon extraction solvent and to separate all such components from the solvent and in the same equipment and then to separate the acid components from the $C_2+$ components in liquid phases.

It is a particular object of this invention to utilize a physical solvent as the preferred hydrocarbon extraction solvent and to utilize a dialkyl ether of polyethylene or polypropylene glycol or mixtures thereof as the preferred physical solvent.

In accordance with these objects, the process of this invention uses dimethylether of polyethylene glycol for extracting ethane and heavier hydrocarbon components and water, if present, from a natural gas stream, at any desired ethane recovery from 2% to 98% while recovering 99+% of propane and all heavier hydrocarbons. Using the same solvent, the process of this invention can achieve any desired propane recovery from 2% to 99+% while recovering 99+% of butanes and all heavier hydrocarbons without recovering more than 2% of ethane. The inlet gas pressure can range from 300 psig to 1300 psig and from an ambient temperature of 75° F. to 120° F.

This process produces a liquid hydrocarbon product having a composition which is selectively versatile rather than fixed, as in prior art processes. In consequence, the composition of its hydrocarbon product can be readily adjusted in accordance with market conditions so that profitability of the absorption operation can be maximized at all times and on short notice.

Such versatility is achieved by flexibility in certain operating conditions and by use of certain additional steps that are not used in the prior art. These conditions and steps are listed as follows, in order of importance:

(1) varying the flow rate of the solvent with respect to flow rate of the natural gas stream;
(2) varying the flashing pressure for one or more of the successive flashing stages;
(3) recycling the flashed $C_1+$ undesirable gases to the extraction column; and
(4) rejecting selected components of the liquid product viz., methane (demethanizing), methane plus ethane (de-ethanizing), methane, ethane, and propane (depropanizing), or methane, ethane, propane, and butanes (debutanizing) in a stripping column for the liquid product by:
 (a) varying the pressure in the column, and
 (b) varying the temperature at the bottom of the column.

When changing process conditions to produce a new liquid product mix in accordance with the needs of the market, an operator must have all four process steps available for consideration. He must consider each of the steps in the order listed, but he need not necessarily change all of them. For some natural gas streams, solvent flow variation and recycling in addition to demethanizing is adequate, for example, and merely changing process steps can sometimes be sufficient. However, for most natural gas streams, optimum efficiency is obtained when all four of the preceding conditions and steps are utilized. It is thereby extremely easy, for example, to recover 99+% of propane and less than 2% of ethane without any additional investment or to recover 99+% of the butanes and less than 2% of the ethane and propane without any additional investment.

Depending upon the liquid product specifications and the inlet natural gas composition, the rejecting step may utilize a single-stage separator, a rectifier, a stripper, or a standard multi-stage distillation column. The generally preferable mode is stripping, wherein emphasis is placed on keeping undesired lighter hydrocarbons from coming down the column.

"Demethanizing" refers strictly to removal of methane from the liquid product entering demethanizer 91 and always occurs as a part of the stripping step. When ethane is additionally removed, such removal may herein be referred to as de-ethanizing; when propane is also removed, such removal may herein be identified as depropanizing; and when butanes are further removed, such removal may herein be described as debutanizing. Nevertheless, the generic term used herein for removal of $C_1$, $C_1+C_2$, $C_1+C_2+C_3$, or $C_1+C_2+C_3+C_4$'s is demethanizing and, unless otherwise qualified, this term is to be understood as encompassing any one of these four removal possibilities.

In a continuous process for separating water and hydrocarbons heavier than methane from an inlet natural gas stream which comprises: (1) extracting the water and the hydrocarbons heavier than methane from the natural gas stream with a physical solvent at pipeline pressures and at a solvent flow rate sufficient to produce rich solvent containing the water, a $C_1+$ mixture of hydrocarbons, and a residue natural gas of pipeline quality which is returned to a pipeline, (2) successively flashing the rich solvent in a plurality of flashing stages at successively decreasing pressures to produce a plurality of successive $C_1+$ gas fractions, having successively lower methane contents, and liquid mixtures of the water, the solvent, and mixtures of hydrocarbons having successively lower methane contents, and (3) regenerating the liquid mixture from the last stage of the flashing stages to produce the physical solvent for the extracting, the improvement which produces a liquid hydrocarbon product having a composition which is selectively adjustable to substantially any selected degree in accordance with market conditions, comprising the capability of utilizing at least one of the following operational procedures:

A. selectively varying the flow rate of the solvent with respect to the flow rate of the natural gas stream during the extracting to adjust the composition of the rich solvent relative to selected components of the group consisting of ethane, propane, and iso and normal butanes;

B. selectively varying the flashing pressures of the successive flashing stages to adjust the composition of the successive gas fractions and the successive liquid mixtures relative to the selected components;

C. recycling at least the first of the successive flashed $C_1+$ gas fractions to the extracting to extract maximum quantities of the ethane and heavier hydrocarbons; and D. demethanizing at least the last of the successive $C_1+$ gas fractions to produce the liquid hydrocarbon product comprising the selected components by:
  (1) selectively varying the pressure of the demethanizing, and
  (2) selectively varying the bottoms temperature of the demethanizing.

If the natural gas stream is sour, it is preferred that it be sweetened by contact with an acid-absorbing solvent, such as an amine, for example, before the absorption process of this invention is utilized. However, if an amine pretreating step is not suitable, the sour natural gas stream can be treated according to the instant process. The acidic components are then maintained in liquid-phase or vapor-phase solution or contact, respectively, with the heavier hydrocarbon components until the solution or mixture, as a liquid, can be contacted by an acid-absorbing solvent. Because such post-absorption sweetening is done in liquid phase, the capital cost for equipment is relatively low.

According to this process, the inlet gas enters the extractor at the bottom and flows upward while liquid solvent enters the extractor near the top and flows downward. The gas and liquid solvent contact one another in any suitable liquid-gas contacting means, such as distillation trays or column packing. The quantity of liquid solvent that is useful is a function of contact area, inlet gas flow rate, gas pressure, composition of $C_2+$ components in the hydrocarbon product, and/or design recoveries of ethane plus heavier hydrocarbon components.

The gas leaving overhead from the extractor meets pipeline specifications. The liquid solvent, rich in ethane plus heavier hydrocarbon components, is let down in pressure in stages in order to reduce energy consumption. In all embodiments described hereinafter, the first stage is represented by a medium-pressure flash tank, wherein some of the methane is flashed and then compressed. The liquid solvent, containing ethane plus heavier hydrocarbon components, is further let down to a lower-pressure flash tank wherein more of the ethane, propane, and some butanes are flashed. These are also compressed.

The composition of the flashed vapor streams varies with the variance of the solvent flow rate into the extractor. The composition of these flash vapor streams also varies according to other changes in the four preceding steps and conditions to obtain desired objectives as to the composition of the liquid products. For example, if $C_3+$ components are desired as the liquid products, relatively small amounts of methane, if any, will be present with the solvent leaving the extractor since the solvent flow rate is reduced to meet operational objectives.

In some embodiments, the liquids from the low-pressure flash tank are again let down to an atmospheric-pressure flash tank, where all the remaining hydrocarbons which are absorbed in the extractor are flashed out of the solvent and compressed, or, in one preferred embodiment, are let down directly to a vacuum flash tank where the remaining hydrocarbons are also flashed out of the solvent. Where an atmospheric flash tank is utilized, a vacuum flash tank may be selectively installed thereafter. A demethanizer column may advantageously be utilized after the vacuum flash tank.

If the inlet gas stream to the extractor contains water, the liquid in the atmospheric flash tank is composed of solvent and water. When the water content of a natural gas stream is high, a preferred solvent is dimethyl ether of polyethylene glycol, since the water solubility relative to methane is 11000 in DMPEG when compared to similar relative solubility of normal heptane of 360. In order to remove this water, the liquid is pumped from the atmospheric flash tank to a solvent regenerator, wherein water is separated overhead while the pure solvent is pumped for recycling back to the extractor. Depending upon the water content of the sweet natural gas and its $C_8+$ hydrocarbon content being fed to the extractor, water may be stripped from the solvent with the help of a stripping gas such as dry compressed air, nitrogen, or methane. If the $C_8+$ hydrocarbon content of the inlet natural gas stream is significant, compressed air may not be suitable due to the need for recovery of such $C_8+$ hydrocarbons in downstream processes and because of safety reasons. Alternatively, a reboiler may be required if such stripping gas is not available. If the inlet sweet gas does not contain any water, the solvent regenerator can be bypassed by recycling the pure solvent from the atmospheric flash tank to the extractor.

The gases leaving the medium-pressure and low-pressure flash tanks, after compression and cooling, are generally returned to the extractor. The gases leaving the atmospheric and vacuum flash tanks are suitably combined, if both of these flash tanks are used, and are then compressed and condensed in a cooler and then stored in a storage vessel as liquids. From this storage vessel, the liquids are pumped to a pipeline if product specifications are met. Alternately, the condensed liquids are further processed in a liquid product column such as a demethanizer whenever undesired components, particularly methane, need to be removed. The off-gas from the demethanizer is compressed, cooled, and returned to the extractor.

In general, the smaller the quantity of $C_5+$ hydrocarbons in the natural gas stream, the higher the final flashing pressure can be. The pressures that are needed in a vacuum tank are in the range of 2 to 25 psia. The quantity of $C_2+$ hydrocarbons also affects the amount of methane that is picked up by the solvent and removed in the demethanizer. In general, the richer the feed in $C_2+$ hydrocarbons, the less the methane pickup will be. Consequently, when treating a very rich feed, a demethanizer is likely not to be needed, provided the liquid composition meets specifications.

The absorption principle leads to an alpha or relative volatility for methane with respect to ethane of slightly less than 5 for almost all known absorption liquids. However, the relative volatility for methane with respect to ethane in the presence of dimethyl ether of polyethylene glycol (DMPEG) is 6.4, indicating that it is more selective toward ethane than other absorption liquids. N-methyl pyrrollidone (NMP) and dimethyl formamide (DMF) have relative volatilities for methane/ethane of 5.3 and 8.5, respectively. However, the solubility of hydrocarbons in NMP is 0.03 standard cubic feet per gallon (SCF/gal) and in DMF is 0.04 SCF/gal; these are low when compared to 1.0 SCF/gal for DMPEG.

Therefore, it is the combination of improved selectivity towards ethane and the hydrocarbon loading capacity of dimethyl ether of polyethylene glycol that makes it a superior absorption solvent for separating and recovering the components of a natural gas stream that are heavier than methane. The minimum qualifications for a physical solvent are a minimum relative volatility of methane over ethane of 5.0 (thereby defining its improved selectivity toward ethane over methane) and a minimum solubility of 0.25 standard cubic feet per gallon of the solvent (thereby defining its hydrocarbon loading capacity). However, the ideal physical solvent would have a selectivity toward ethane over methane as high as 10.0, and simultaneously would possess a hydrocarbon loading capacity of about 3.0 SCF/gal. This combination also enables solvent flow rate variation and flashing-pressure variations to be particularly useful for flexibly producing liquid products, having selected hydrocarbon compositions.

The most suitable range of molecular weight for dimethyl ether of polyethylene glycol is 146 to 476, containing 3–10 ethylene units. The glycol can be branched, such as polypropylene glycol. The basic difference between the behaviors of ethyl and propyl groups is the affinity for water for the ethyl and greater affinity for hydrocarbons for the propyl group. A mixture of dimethyl ethers of polyethylene and polypropylene glycol in various combinations is consequently suitable for recovering ethane plus heavier hydrocarbons from a natural gas. In such a mixture, the content of dialkyl ether of polyethylene glycol should be a minimum of 20% by volume, with dialkyl ether of polypropylene glycol being limited to 80% by volume maximum.

$CO_2$ and $H_2S$ have solubilities in DMPEG that are very close to the solubilities of propane and pentane in this solvent. Therefore, it is difficult to separate these acidic materials from the desirable gases when treating sour natural gas. The prior art has tended to perform this separation before removing hydrocarbons, thereby requiring large-capacity equipment and losing significant quantities of desirable hydrocarbons with $CO_2$ and $H_2S$ vent streams. Widespread usage of DMPEG has obviously been avoided.

In one of the embodiments of this invention, $CO_2$ and $H_2S$ are allowed to remain with the desirable gases until final stages in the process where they are removed as liquids, thereby requiring smaller and less expensive equipment because the equipment's size is determined by mode of treating, i.e., in gas phase or liquid phase.

This treatment procedure requires the usage of substantially larger quantities of DMPEG than has been recommended by the prior art, since the quantity of $C_2+$ hydrocarbons is generally larger than the quantities of $CO_2$ and $H_2S$ in a relatively sweet natural gas stream. There is, consequently, enough absorption capacity in the DMPEG stream when equilibrium is reached that the acidic materials in the recycle stream and in the sour natural gas can be completely removed, thereby producing a sweet methane-rich stream from the top of the extractor that meets pipeline specifications.

The advantage of this treatment method over those of the prior art is that a single plant can accept a very wide variety of natural gas streams, from very acidic to completely sweet, simply by utilizing the acid removal unit (e.g., an amines process) to a selective extent or even by by-passing it entirely. Although liquid-phase sweetening requires a lower capital investment and has lower operating costs than gas-phase sweetening, there are compensating factors in favor of gas-phase sweetening. These include the use and pumping of smaller quantities of solvent and the availability of maximum flexibility as to hydrocarbon composition in the liquid product.

It is preferred that amine processes (MEA, DEA, or DGA) be utilized for removing acid gas components ($CO_2$ and $H_2S$) in gas phase before proceeding with this invention process. The sweet natural gas thus produced will be saturated with water vapor at the pipeline pressures and operating temperatures because any amine process is aqueous based and introduces water vapor into the natural gas stream.

Alternatively, acid gas components can be removed in the liquid phase downstream of processing according to this invention process by amine processes using MEA or DEA. For maximum flexibility of recovering ethane versus rejecting ethane while recovering all of propane plus heavier hydrocarbons in contrast to recovering propane versus rejecting ethane and propane while recovering all of butane plus heavier hydrocarbons, it is preferred that the sour natural gas stream be treated with aqueous amine processes in gas-phase operation in order to extract $CO_2$ and $H_2S$ components without losing any hydrocarbons.

The advantages of this invention are as follows:
1. low capital investment;
2. low energy and operating costs;
3. low maintenance requirements;
4. no special metallurgical requirements;
5. reduced environmental emissions;
6. simplicity in operation, even permitting unattended operation;
7. operability in remote locations where water is not available;
8. no freeze-up problems caused by cold temperature;

9. optimum operation at essentially ambient temperature so that minimal to no insulation is required;
10. minimum need for heat exchange so that no fouling of equipment occurs;
11. suitable operation at pipeline pressure even during pressure swings;
12. no need for catalyst, chemicals, inhibitors, or additives;
13. minimal to no need for refrigeration;
14. extremely flexible, wide range of ethane recoveries without additional equipment, based on market economics, such recoveries varying from as high as 98% to as low as 2%; i.e., operation can vary from ethane recovery to ethane rejection;
15. constant level of propane recovery of 99+%, even at low ethane recovery of 2%;
16. extremely flexible, wide range of propane recoveries without additional equipment, based on market economics, such recoveries varying from as high as 99% to as low as 2%, i.e., operation can vary from propane recovery to propane rejection;
17. constant level of butanes recovery of 99+%, even at low propane recovery of 2%;
18. continuous operation with no cycling of drier beds for drying and regeneration; and
19. no need to dry the gas to 1 ppm $H_2O$ because no cryogen is required in the process.

When dialkyl ethers of polyalkylene glycol are the solvent, the advantages are additionally as follows:

1. solvent is non-toxic, biodegradable, and environmentally acceptable;
2. solvent is non-corrosive, non-foaming, non-degrading, and hygroscopic;
3. solvent has extremely low vapor pressure, e.g., 0.002 mm Hg at 77° F., resulting in minimum solvent losses;
4. solvent does not require mixing with any other base, so that no compositions need be maintained for extraction of liquid hydrocarbons;
5. solvent has high loading capacity, thereby minimizing its circulation rate;
6. dry or water-saturated inlet gas streams can be processed; and
7. solvent is capable of completely removing acidic components from a sour natural gas stream.

BRIEF DESCRIPTION OF THE DRAWINGS

The invention may be more readily understood by referring to the drawings which diagrammatically illustrate preferred embodiments for treating both sweet and sour natural gases for removal of water and hydrocarbons heavier than methane from a well-head natural gas stream.

DESCRIPTION OF THE PREFERRED EMBODIMENTS

Figure 1:
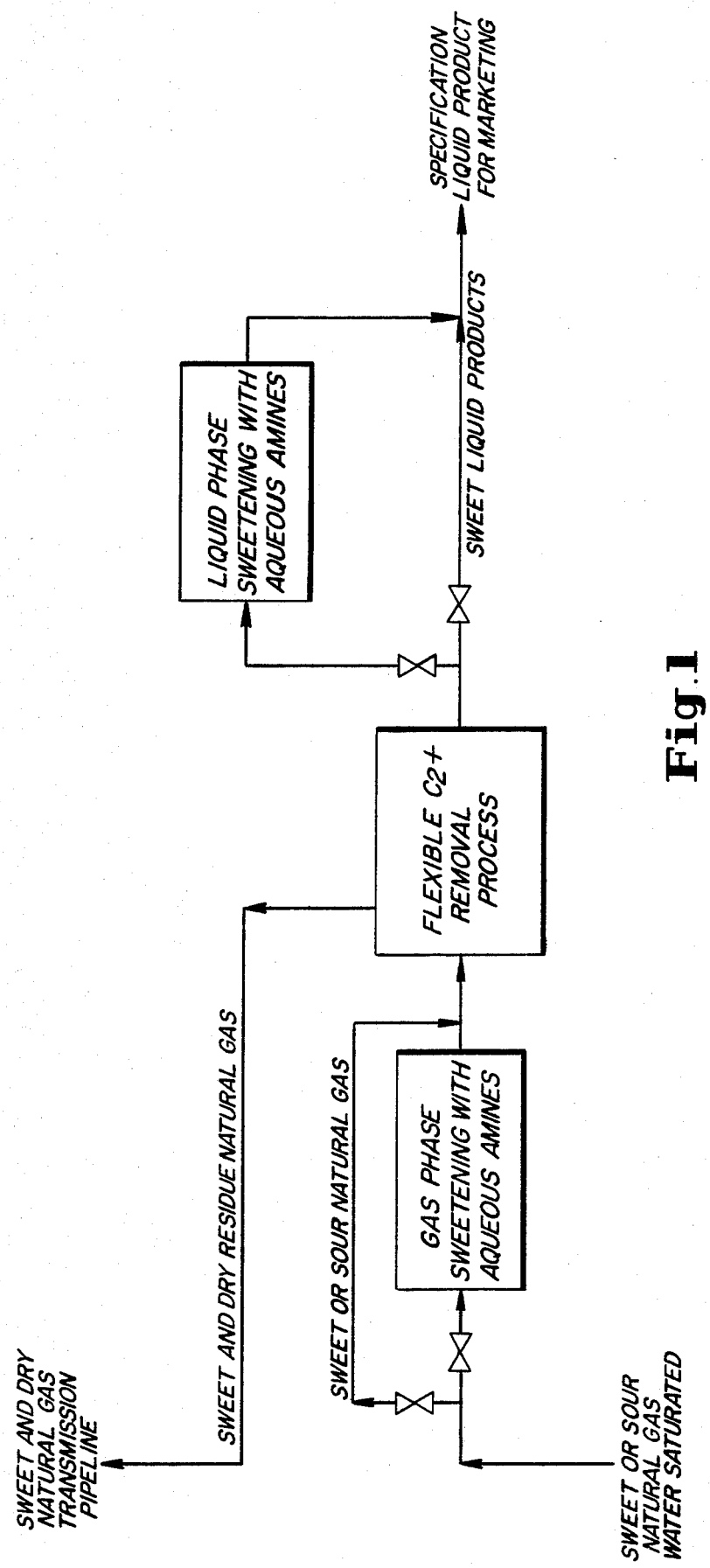
FIG. 1 is an overall schematic flow sheet illustrating the utilization of the flexible process of this invention for selectively recovering $C_2+$, $C_3+$, or $C_4+$ hydrocarbons from a natural gas stream, sweet or sour, and having any water content up to saturation.
Figure 2:
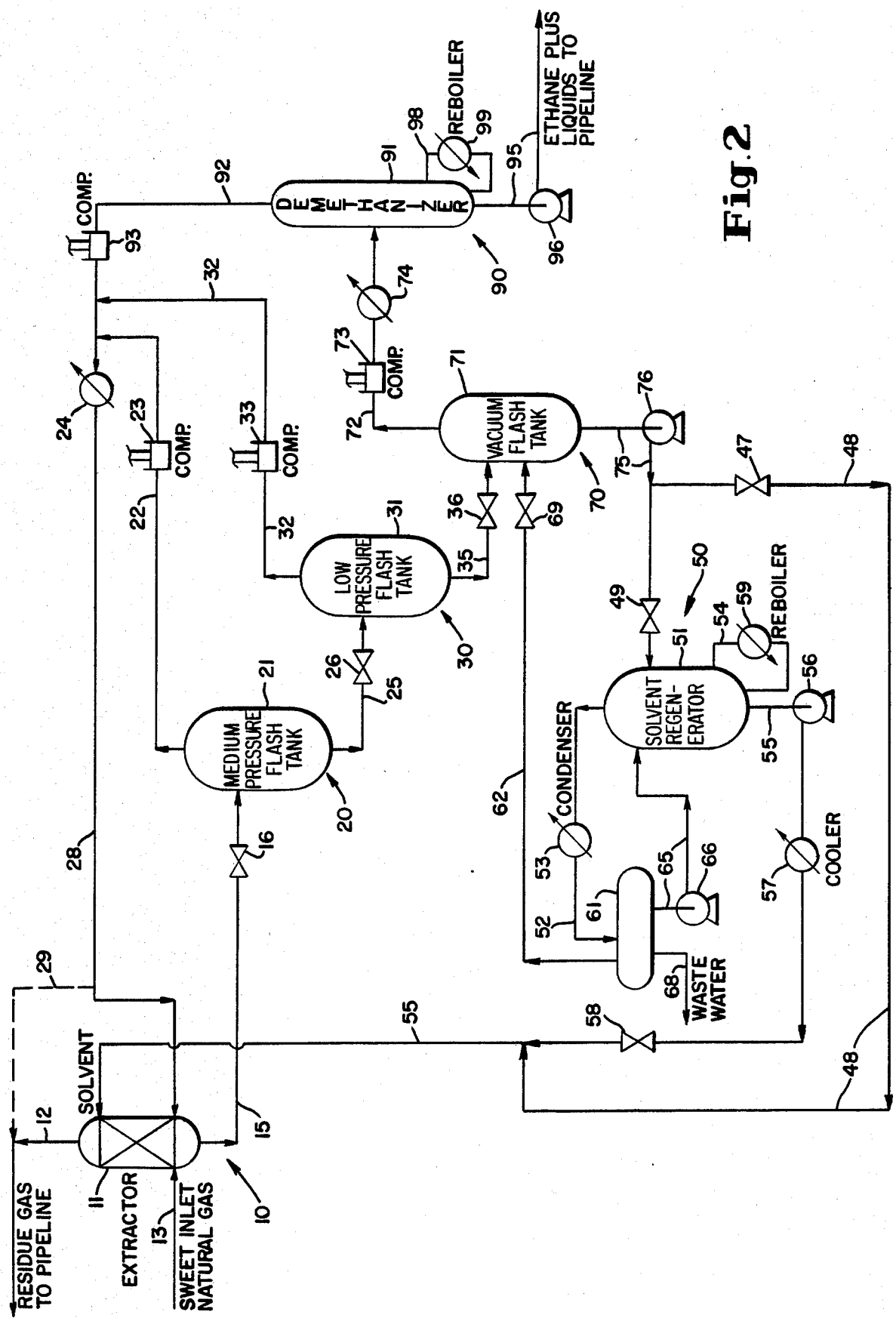
FIG. 2 is a schematic flow sheet for extraction of a recycle stream and a sweet inlet natural gas stream at 300–1300 psig with dimethyl ether of polyethylene glycol (DMPEG), and recovery of liquefied $C_2+$ hydrocarbons by using three flashing stages and a demethanizer.

The process shown schematically in the flow sheet of FIG. 2 comprises an extraction (absorption) unit 10, a medium pressure flash unit 20, a low pressure flash unit 30, a vacuum flash unit 70, a regenerator unit 50, and a demethanizer unit 90.

Referring to FIG. 2, sweet natural gas at 300–1300 psig is introduced through line 13 into extractor 11 which may be any suitable tower which is filled with packing or contains perforated plates or bubble plates. Solvent enters through line 55 near the top of extractor 11, and residue gas is discharged through line 12 to the pipeline at 300–1300 psig. The rich solvent in line 15 contains water, methane, and other hydrocarbon components heavier than $CH_4$. The solvent in line 55 is a normally liquid dialkyl ether of a polyalkylene glycol, preferably polyethylene glycol dimethyl ether having 3 to 10 ethylene units and a molecular weight of 146 to 476, which is substantially dehydrated for maximum dehydration capacity.

Extractor 11 is maintained at about 20°–120° F., preferably 70°–80° F. Solvent is fed through line 55 at a rate sufficient to reduce the water content of the sweet natural gas leaving through line 12 to less than 12 pounds per million standard cubic feet and preferably to less than 7 pounds per million standard cubic feet. Under these conditions, the ethane and other hydrocarbon components of greater molecular weight in line 12 are reduced to a very low value. By altering the amount of solvent entering through line 55, the proportion of ethane to the predominant methane may be varied at will, but the solvent ratio is usually at 0.005 to 0.5 gallon of solvent per standard cubic foot of inlet natural gas, whether sweet or sour.

The rich solvent in line 15 passes through valve 16, enters medium-pressure flash tank 21 from which primarily methane and some heavier hydrocarbons are discharged through line 22, being then compressed by compressor 23 to a slightly higher pressure than the pressure in the natural gas stream. A mixture of solvent, hydrocarbon components, and water is discharged through line 25 and valve 26 and enters low-pressure flash tank 31 from which a mixture of additional methane and some heavier hydrocarbons is discharged through line 32, being compressed by compressor 33 to the same pressure as created by compressor 23. A mixture of solvent, remaining methane, ethane and heavier hydrocarbons, and water is discharged through line 35 and valve 36 into vacuum flash tank 71 from which substantially all of the remaining hydrocarbons are discharged through line 72. This mixture is then compressed by compressor 73 to the operating pressure of demethanizer 91, cooled and condensed by condenser 74, and fed to demethanizer 91. A mixture of solvent, water, and trace quantities of hydrocarbons is discharged from vacuum flash tank 71 through line 75, pumped by pump 76 through valve 49, and sent to solvent regenerator 51.

Solvent regenerator 51 is illustrated as utilizing a reboiler 59 which heats solvent, taken from the bottom of regenerator 51 and passing through line 54, in order to supply heat to the regenerator. The vaporized mixture of trace hydrocarbons and water passes from the top of regenerator 51 through line 52, is condensed in condenser 53, and enters settler 61 from which water is discharged through line 65 and pump 66 to return to regenerator 51 as reflux. Waste water is discharged through line 68. The hydrocarbon vapors from settler 61 leave through line 62, are let down in pressure through valve 69, and enter vacuum flash tank 71. Water-free solvent is discharged from regenerator 51 through line 55 and pump 56, cooled in cooler 57 through valve 58, and returned to enter extractor 11. If the inlet natural gas entering the system through line 13 does not contain water, the solvent in line 75 after pump 76 can bypass regenerator unit 50 through line 48 and valve 47 to join solvent return line 55 to extractor 11.

When the inlet natural gas stream is low in water content, rich solvent stream 15 can contain relatively small quantities of water at equilibrium. Stream 75 can consequently be sufficiently low in water content that passage through regenerator unit 50 is not necessary. Valve 49 is therefore closed, valve 47 is opened, and the solvent stream in line 75 is bypassed through line 48 to line 55.

The mixture of methane, ethane, propane, and heavier hydrocarbons in line 72 passes through compressor 73 and condenser/cooler 74 to demethanizer 91. Methane leaves demethanizer 91 through line 92, is compressed to a pressure slightly higher than pipeline pressure by compressor 93, is joined by the compressed mixture in line 32 and by the compressed methane with some heavier hydrocarbons in line 22, is cooled by heat exchanger 24, and passes through line 28 to enter extractor 11, thereby recycling the methane-rich recovered gas through the extractor. Depending upon the liquid product specification for stream 95 and the desired recoveries of ethane and propane, the combined recycle gases in stream 28 may bypass extractor unit 10 through line 29.

The temperature at the bottom of demethanizer 91 is controlled by providing heat through reboiler 99 and returning the heated bottom liquid through line 98 to demethanizer 91. The liquid meeting the product specifications as to undesirable components (in this situation, methane) leaves the process through line 95 and pump 96 for pipeline shipments.

Figure 3:
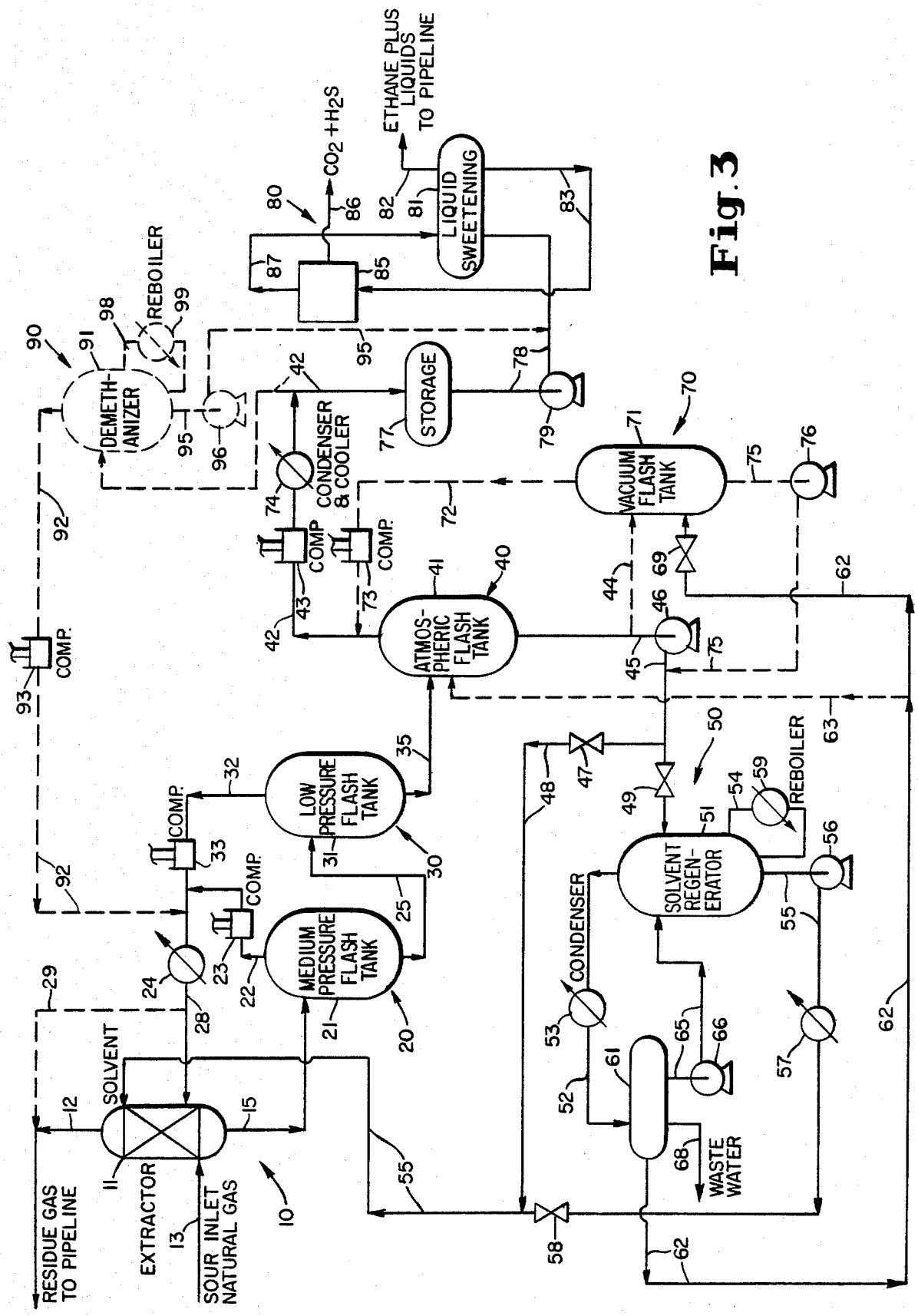
FIG. 3 is a schematic flow sheet for extraction with DMPEG of a recycle stream and a sour inlet natural gas stream at 300–1300 psig with DMPEG and recovery of liquefied $C_2+$ hydrocarbons by using four flashing stages, if necessary, with flashed products from the last two stages being compressed, condensed, and stored in a storage tank. The liquid hydrocarbons containing acid gas components are treated in a tail end unit using amines. Depending upon the liquid product specifications, the liquid product may be demethanized before treating in the amine unit.

FIG. 3 relates to processing a sour natural gas which is received at the same range of pressures as the sweet natural gas treated according to the process of FIG. 2. As seen in the schematic flow sheet of FIG. 3, extractor unit 10, medium pressure flash unit 20, low pressure flash unit 30, vacuum flash unit 70, and solvent regenerator unit 50 are combined exactly as in FIG. 2 and are utilized for the same purposes. However, an atmospheric flash unit 40 is interposed between low pressure flash unit 30 and vacuum flash unit 70, and a sweetening unit 80 follows atmospheric flash unit 40 and vacuum flash unit 70. Moreover, demethanizer unit 90 is shown as an alternate arrangement in the process of FIG. 3; the flashed vapors from medium pressure flash tank 21 and low pressure flash tank 31 are instead returned directly to extractor 11.

Depending upon the liquid product specifications, a demethanizer unit 90, similar to the demethanizer used in the process of FIG. 2, may be added to process the hydrocarbon mixture from line 42 and for returning the undesirable components through line 92 and compressor 93 to join line 28 before cooler 24 for returning the mixture to extractor 11. The liquid leaving the demethanizer 91 can be treated similarly to the liquid product from line 78 after pump 79 through a sweetening unit 80.

Specifically, the solvent stream in line 35 from low pressure flash tank 31 enters atmospheric flash tank 41, producing an overhead gas stream passing through line 42, compressor 43, and condenser/cooler 74 to enter storage tank 77.

If the inlet natural gas in line 13 is relatively lean or has trace quantities of $C_5+$ hydrocarbons, the solvent discharge from tank 41 moves through line 45, pump 46, and valve 49 to enter solvent regenerator 51 where it is processed as described for FIG. 2, except that the hydrocarbon vapors from settler 61 are routed via lines 62 and 63 to atmospheric flash tank 41. However, if the converse is true and the inlet gas is indeed high in $C_5+$ hydrocarbons, the bottoms from tank 41 move through line 44 to enter vacuum flash tank 71. The overhead therefrom passes through line 72 and compressor 73 to join line 42. The bottoms from vacuum flash tank 71 passes through line 75 and pump 76 to join line 45.

From storage tank 77, the liquid $C_2+$ hydrocarbons containing acid components moves through line 78 and pump 79 to amines contactor 81 which produces a sweet product in line 82, consisting essentially of ethane plus heavier hydrocarbon liquids for pipeline shipment. The sour amines stream in line 83 is stripped in unit 85, producing a $CO_2$ and $H_2S$ stream leaving through line 86. The sweet amines stream returns to contactor 81 by line 87.

Simultaneous removal of acid gases and $C_2+$ hydrocarbons from a natural gas stream is not a problem. However, when simultaneously removing $H_2S$ and $CO_2$ with the $C_2+$ hydrocarbons, the hydrocarbons recovered need some form of treatment before shipping as specification product. As discussed in U.S. Pat. No. 3,770,622 with respect to propylene carbonate as the solvent, the $CO_2$ along with hydrocarbons can be vented as a waste stream from a separator while the hydrocarbons heavier than butanes that have gasoline value remain in the separator as a liquid layer which can be decanted. This hydrocarbon loss in the process of U.S. Pat. No. 3,770,622 cannot be avoided because propylene carbonate is a "physical" solvent. In order to minimize this loss of hydrocarbons with the $CO_2$ vent stream, it is necessary to treat all of the hydrocarbons in the vent stream with a chemical solvent such as an aqueous amine solution which chemically reacts with the $CO_2$ in the vent stream.

Since DMPEG is also a "physical" solvent, $CO_2$ and $H_2S$ co-exist with the desirable hydrocarbons. The invention process, as described in FIG. 3, does not produce a separate $H_2S$ and $CO_2$ stream from storage tank 77 wherein the $CO_2$ and $H_2S$ are in contact with hydrocarbon liquids. Therefore, the $CO_2$ and $H_2S$ are chemically removed from the liquid hydrocarbon stream containing these acidic components by treating it with aqueous amine solutions in liquid sweetening unit 80.

As described earlier, cryogenic turbo-expander technology is used to obtain very high ethane recoveries. In order to carry out such extraction from inlet gas streams containing high amounts of $CO_2$ (greater than 0.75 MOL %), it is very important to remove $CO_2$ from the gas stream before subjecting it to cryogenic temperatures in order to avoid $CO_2$ freeze-up problems in the equipment. It is also more desirable to remove acid gases in liquid phase than in gaseous phase because of savings of capital and operating costs.

With the process of this invention, it is possible to remove ethane plus hydrocarbons from a relatively rich $CO_2$ stream without freezing problems and to remove $CO_2$ from desirable liquids in the liquid phase by using known amines.

As taught, for example, in U.S. Pat. No. 4,070,165, suitable sweetening amines are monoethanolamine (MEA), diethanolamine (DEA), di-isopropanolamine (DIPA), and diglycolamine (DGA). Although it is common practice to utilize amines in an aqueous solution ranging from 15% to 70% by weight, it may be preferred to utilize another solvent, such as methanol or acetone, for forming the amine solution circulated in amine unit 80 of this invention.

Other known sweetening processes which are suitable for treating the $C_2+$ products in storage tank 77 are also satisfactory. Particularly suitable processes are those which utilize a solid-bed dessicant, such as activated alumina, silica gel, silica-alumina beads, and molecular sieves.

Figure 4:
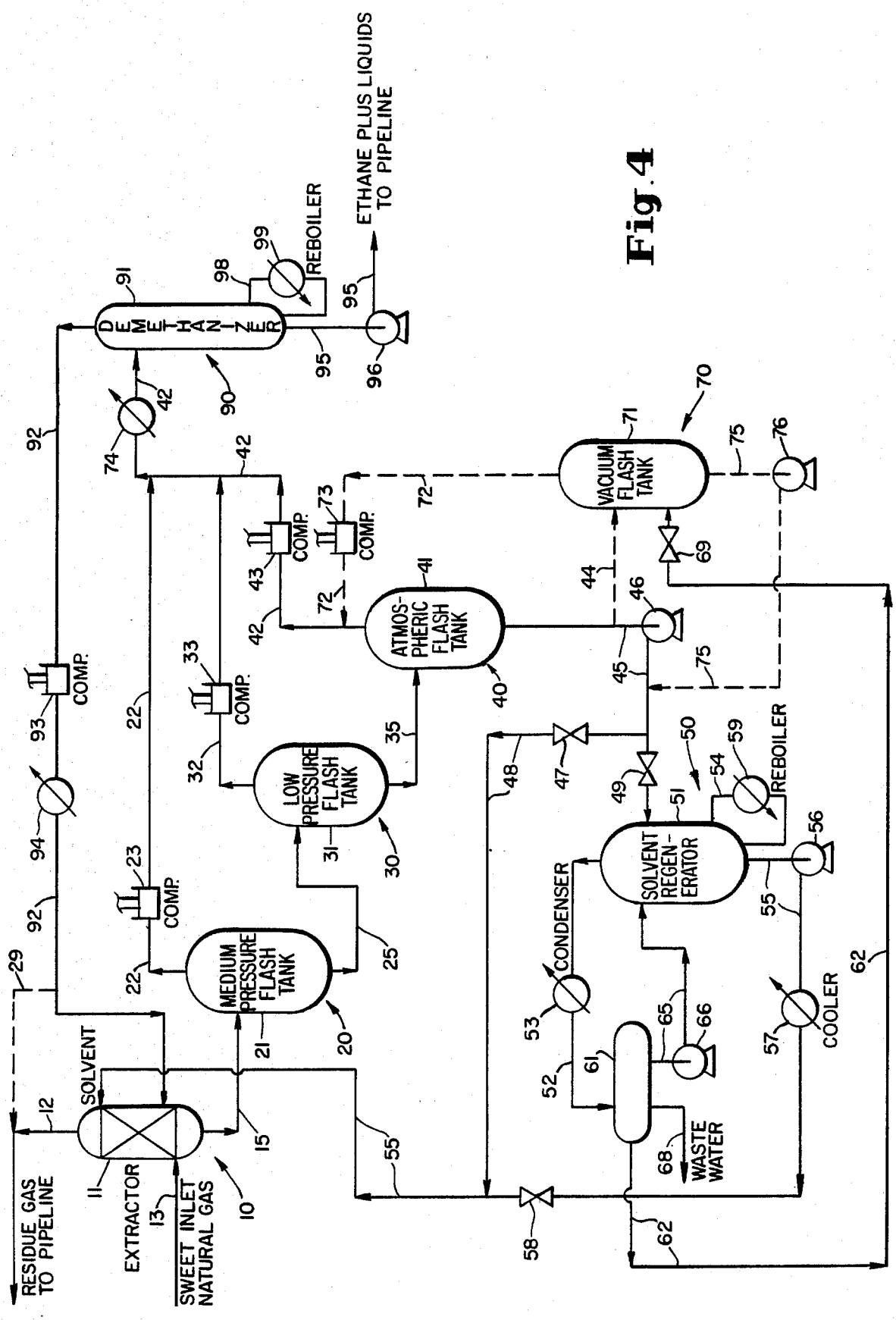
FIG. 4 is a flow sheet which is exactly the same as FIG. 2 except that there are four flashing stages, if necessary, all of the flashed products being fed to the demethanizer and only the overhead of the demethanizer being recycled directly to the extractor.

The process shown schematically in the flow sheet of FIG. 4 is directed to treating sweet inlet natural gas at 300–1300 psig and is very close to that of FIG. 2 in that it comprises an extractor unit 10, a medium pressure flash unit 20, a low pressure flash unit 30, a vacuum flash unit 70, a solvent regenerator unit 50, and a demethanizer unit 90. However, it additionally comprises an atmospheric flash unit 40, as in FIG. 3.

Unlike either FIG. 2 or FIG. 3, moreover, overhead discharge line 22 and overhead discharge line 32 join overhead discharge line 42, which is previously joined by overhead vacuum discharge line 72 (if unit 70 is utilized), so that all products from units 20,30,40, and 70 enter demethanizer unit 90. Demethanizer 91 and reboiler 99 must be larger, in consequence, than in the process of FIG. 2 or FIG. 3 for the same inlet quantity of sweet or sour natural gas entering through line 13. On the other hand, all products of units 20,30,40, and 70 are treated alike, and very small quantities of $C_2+$ hydrocarbons are retained by the gas leaving in line 12.

The off gases from demethanizer 91 leave through overhead discharge line 92, are brought up to pipeline pressure in compressor 93, cooled in condenser 94, and returned to the lower portion of extractor 11.

Figure 5:
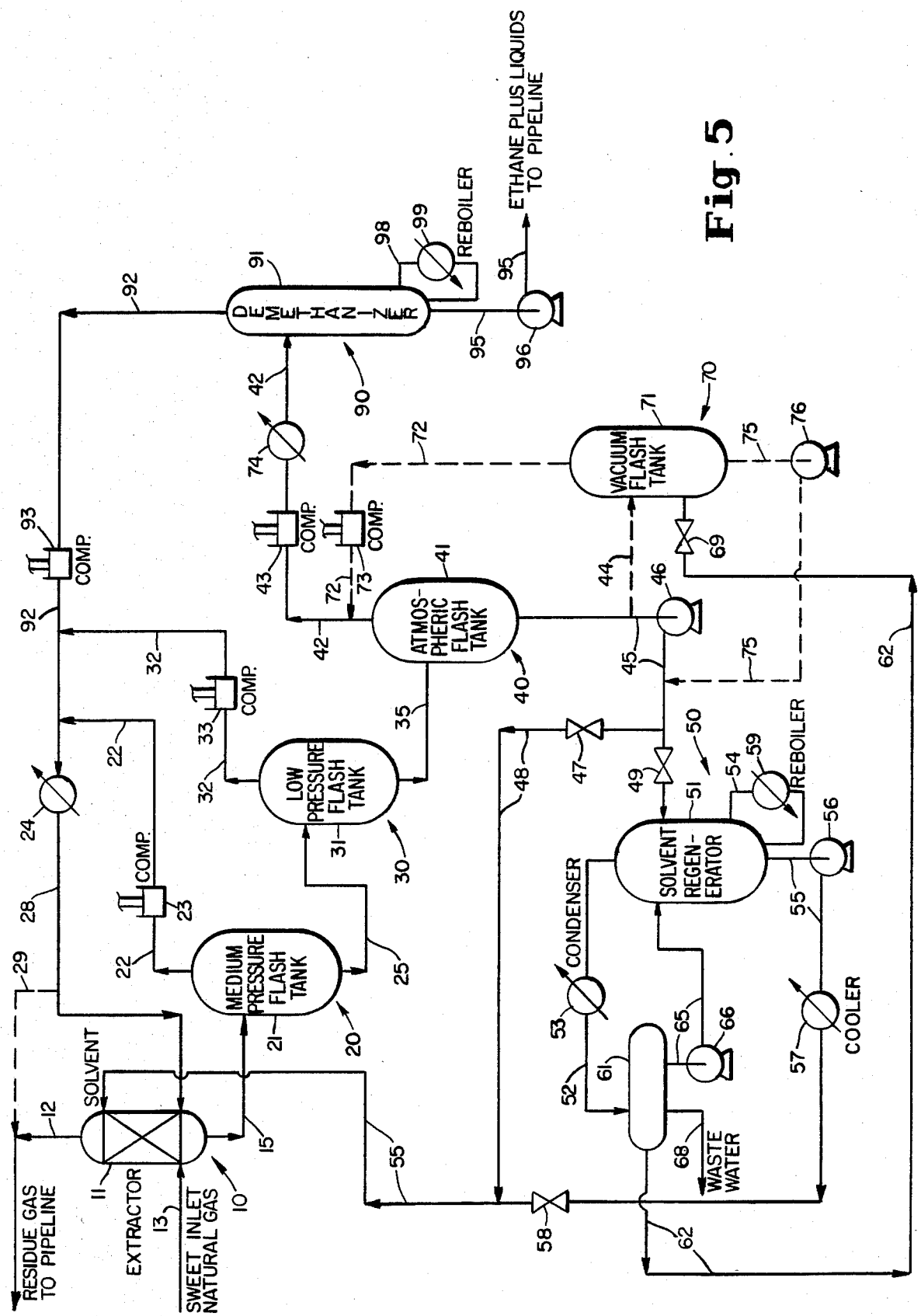
FIG. 5 is a flow sheet which is exactly the same as FIG. 4 except that the flashed products of the first two stages bypass the demethanizer and are recycled directly to the extractor.

The process shown schematically in the flow sheet of FIG. 5 is directed to treating sweet inlet natural gas at 300–1300 psig which enters extractor 11 through line 13. The process includes extractor unit 10, medium pressure flash unit 20, low pressure flash unit 30, atmospheric pressure flash unit 40, vacuum flash unit 70, solvent regenerator unit 50, and demethanizer unit 90, so that it is exactly like the process of FIG. 4 except that discharge lines 22 and 32 join discharge line 92 for cooling of all compressed products in condenser 24 and returning them to extractor 11 in combined line 28.

Even though only four schematic arrangements have been illustrated and described hereinbefore, it should be recognized that the process steps are important and that they can be arranged in a multitude of combinations consistent with the operational objectives and given market conditions. The invention process is extremely flexible and cannot be limited to the schematic arrangements shown.

It is extremely important to note that the high ethane plus heavier hydrocarbon recoveries are achieved by closing the loop around the process; as such, any $C_2+$ components leaving through overhead streams of medium, low, and atmospheric pressure flash tanks along with vapors from the vacuum tank and demethanizer overheads get a second chance at recovery through the extractor 11 in all four schematic arrangements. It is this key factor that allows the achievement of unusually high recoveries. This provides another degree of freedom in process design that is not available in any of the natural gas liquids extraction processes described earlier.

Another important element that is unique to this invention is the ability to select and set a pressure in each of the intermediate flashes from medium to vacuum tanks, based on economic objectives for a given stream. The pressures are chosen such that all undesirable components, after adjusting the solvent rate to extractor 11 through line 55, are flashed off and recycled back to extractor 11 in order to recover desirable components in high yield from the recycle stream. The feed forward streams to demethanizer system 90 are composed primarily of desirable components for stream 95.

Controlling the temperature at the bottom of demethanizer 91 through reboiler 99 also enables specific undesirable components to be selectively rejected. Such components are methane, ethane, propane, or butane, depending upon the operational objectives and existing market conditions.

The operating pressure of demethanizer unit 90 can also be varied at will, consistent with the operational objectives, thereby operating the same equipment as a deethanizer if $C_3+$ product is desired, as a depropanizer if $C_4+$ product is desired, or as a debutanizer if $C_5+$ product is desired, instead of using it as a demethanizer. The operating pressure in demethanizer unit 90 can vary from 50–450 psia.

The factor that allows unusually high hydrocarbon recoveries and extremely flexible degree of component selectivity is essentially the recognition of gas solubility and loading capacity characteristics of the various solvents, such as DMPEG. Due to significant departures among the solubilities of ethane, propane, iso and normal butanes, iso and normal pentanes, hexane, heptane, etc., relative to methane, the desired hydrocarbons can be selectively recovered from a natural gas stream by adjusting the solvent flow rate to extractor 11 through line 55, recycling flashed gas mixtures to extractor 11, and adjusting the operating pressure levels in the intermediate flash tanks 20, 30, 40, and 70, and in demethanizer unit 90.

All the invention processes described in FIGS. 2, 4, and 5 have only one inlet hydrocarbon stream 13 and two outlet streams 12 and 95, with outlet stream 29 being additionally available when stream 28 contains no components that need to be recovered. The process described in FIG. 3 has the same inlet stream 13, which contains acid gases, $CO_2$ and $H_2S$, that are removed by an aqueous amine solution through line 86. All of the hydrocarbon components entering the process through line 13 leave either through line 12 or line 82, with line 29 available to bypass the extracting step when line 28 contains no components that need to be recovered. In all the described embodiments, no hydrocarbons are lost.

EXAMPLE I

An ethane recovery plant, utilizing the process of FIG. 2, is designed and put into operation to treat one million standard cubic feet per day (1 MMSCFD) of dry sweetened natural gas for 95% ethane recovery. The composition of the natural gas entering extractor 11 of extractor unit 10 is as follows:

| Component | MOL % |
| --- | --- |
| Nitrogen | 2.02 |
| Methane | 80.62 |
| Ethane | 9.69 |
| Propane | 4.83 |
| ISO-Butane | 0.50 |
| N—Butane | 1.45 |
| ISO-Butane | 0.30 |
| N—Pentane | 0.37 |
| Hexane Plus | 0.22 |
| | 100.00 |

Water Content 169 lbs/MMSCF dry gas
Inlet Pressure 625 psia
Inlet Temperature 120° F.

Sweetened natural gas stream 13 enters extractor 11 near its bottom. A recycle stream 28 also enters the extractor near the bottom. The combined gases from streams 13 and 28 flow upward in the extractor where they are contacted by lean solvent stream 55 flowing downwards. The molar ratio of solvent to fresh feed stream 13 is of the order of 1.36:1.00. Ethane and heavier liquids present in the inlet gas stream are selectively absorbed and removed from the extractor by stream 15. The remaining natural gas leaves the extractor through stream 12 which is primarily composed of nitrogen, methane, and small amounts of ethane, depending upon the desirable recoveries of ethane. Virtually all of the propane and heavier components are removed from stream 13. Stream 15 contains about 2.1 times as many moles of methane as moles of ethane.

In order to remove methane from recovered hydrocarbons while conserving energy consumption, the pressure of stream 15 is let down from 625 psia to 400 psia in medium pressure flash tank 21 wherein vapor stream 22, rich in methane (about 88 MOL % methane), is separated from liquid stream 25 which contains about 30% less methane and about 94% of the ethane present in stream 15. Stream 22 is compressed from 400 psia to 630 psia for recycle back to the extractor via stream 28.

In order to further reduce the amount of methane which is associated with ethane, the liquid pressure is reduced from 400 psia to 300 psia in low pressure flash tank 31. Here stream 32, consisting of about 86 MOL % methane, is separated from liquid stream 35 which contains about 1.19 moles of methane per mole of ethane and has about 51% less methane than the amount of methane present in stream 15. Vapors leaving via stream 32 are compressed to 630 psia for recycle to extractor 11 via stream 28.

In order to separate all hydrocarbon components from the solvent, the pressure of liquid stream 35 is reduced from 300 psia to 5 psia in a vacuum flash tank 71. The hydrocarbon vapors leaving tank 71 via stream 72 are compressed to 400 psia in compressor 73 and cooled to 20° F. in condenser 74 to condense ethane plus heavier hydrocarbons. Some methane also gets condensed and is stripped by demethanizer 91. The demethanized liquid product meeting specifications leaves the process via stream 95. The stripped methane from stream 72 leaves demethanizer 91 via stream 92 and is compressed to 630 psia for recycle to extractor 11 via stream 28. The combined streams 22, 32, and 92 are cooled to about 120° F. and recycled to extractor 11 via stream 28.

Depending upon the ethane recovery requirements, it may or may not be necessary to recycle stream 28 to the extractor. Instead, stream 28 can bypass the extractor and leave the plant as stream 29 by joining stream 12, as shown in FIGS. 2, 3, 4, and 5. The amount of methane that is present in stream 15 depends upon the partial pressures of desirable hydrocarbon components in stream 13.

Liquid stream 75 leaving vacuum flash tank 71 contains about 1.5 MOL % hydrocarbons and water, with the rest being the solvent. This stream is pumped into solvent regenerator 51 where contained water and hydrocarbons are separated overhead. The solvent regenerator operates typically at about 20 psia. The solvent is heated to about 300° F. to completely remove water from the solvent in the solvent regenerator and is cooled to about 120° F. before returning it to the extractor via stream 55. However, the water content of solvent stream 55 can be 2-15 wt. % without causing any detrimental effect on the performance of the extractor.

The water is separated from the hydrocarbon vapors in column overhead accumulator 61 and is used as reflux through line 65 for solvent regenerator 51. Excess water leaves the process through stream 68. The hydrocarbon vapors are recycled under its pressure via stream 62 to vacuum flash tank 71. However, in a process wherein an atmospheric flash tank 41 is used, as in FIG. 3, the hydrocarbon vapors may be routed via lines 62 and 63 to atmospheric flash tank 41 instead of to vacuum flash tank 71.

The operation of the process as depicted in FIG. 2 can be more clearly understood by study of the compositions of the various streams in pound-mols per hour (LB-MOLS/HR). Eleven components of 15 streams are given in the following two tables.

It is apparent from these tables that about 30% of the 25.76 pound-mols/hr of methane that is dissolved in solvent stream 15 is returned to extractor 11 in stream 22, about 21% is returned in stream 32, and about 48% is returned in stream 92. With respect to the 12.09 pound-mols/hr of ethane that leave in solvent stream 15, about 6.2% is returned to extractor 11 in stream 22, 5.9% is returned to extractor 11 in stream 32, 4.5% is returned in stream 92, and 83.4% leaves in product stream 95. With respect to the 5.60 pound-mols/hr of propane in stream 15, 2.7% returns in stream 22, and 2.7% returns in stream 32 to extractor 11 via line 28 while 94.6% leaves in product stream 95.

Without employing demethanizer unit 90, as in FIG. 3, it is clear that about half of the methane can become part of the product stream in line 82. Nonetheless, economic considerations, based upon product specifications, may easily obviate a need for demethanizer unit 90. Moreover, other design considerations may be important. For example,

TABLE I

MATERIAL BALANCE FOR ILLUSTRATIVE EXAMPLE

| Components Lb-Mols/Hr | Stream No. | | | | | | |
|---|---|---|---|---|---|---|---|
| | 13 | 55 | 12 | 15 | 28 | 22 | 25 |
| Nitrogen | 2.22 | — | 2.22 | 0.11 | 0.11 | 0.07 | 0.04 |
| Methane | 88.48 | — | 88.26 | 25.76 | 25.54 | 7.69 | 18.07 |
| Ethane | 10.63 | — | 0.54 | 12.09 | 2.00 | 0.75 | 11.34 |
| Propane | 5.30 | — | Trace | 5.60 | 0.30 | 0.15 | 5.45 |
| ISO-Butane | 0.55 | — | — | 0.57 | 0.02 | 0.01 | 0.56 |
| N—Butane | 1.59 | — | — | 1.63 | 0.04 | 0.02 | 1.61 |
| ISO-Pentane | 0.33 | — | — | 0.33 | — | — | 0.33 |
| N—Pentane | 0.41 | — | — | 0.41 | — | — | 0.41 |
| Hexane Plus | 0.29 | — | — | 0.29 | — | — | 0.29 |
| Water | 0.39 | — | — | 0.39 | — | — | 0.39 |
| Solvent | — | 150.0 | — | 150.00 | — | — | 150.00 |
| TOTAL, LB-MOLS/HR | 110.19 | 150.00 | 91.02 | 197.18 | 28.01 | 8.69 | 188.49 |

TABLE II

MATERIAL BALANCE FOR ILLUSTRATIVE EXAMPLE

| Components, Lb-mols/Hr | Stream No. | | | | | | | |
|---|---|---|---|---|---|---|---|---|
| | 32 | 35 | 72 | 75 | 92 | 95 | 68 | 62 |
| Nitrogen | 0.02 | 0.02 | — | — | 0.02 | — | — | — |
| Methane | 5.39 | 12.68 | 12.68 | 0.09 | 12.46 | 0.22 | — | 0.09 |
| Ethane | 0.71 | 10.63 | 10.63 | 0.44 | 0.54 | 10.09 | — | 0.44 |
| Propane | 0.15 | 5.30 | 5.30 | 0.51 | Trace | 5.30 | — | 0.51 |
| ISO-Butane | 0.01 | 0.55 | 0.55 | 0.09 | — | 0.55 | — | 0.09 |
| N—Butane | 0.02 | 1.59 | 1.59 | 0.31 | — | 1.59 | — | 0.31 |
| ISO-Pentane | — | 0.33 | 0.33 | 0.10 | — | 0.33 | — | 0.10 |
| N—Pentane | — | 0.41 | 0.41 | 0.15 | — | 0.41 | — | 0.15 |
| Hexane Plus | — | 0.29 | 0.29 | 0.13 | — | 0.29 | — | 0.13 |
| Water | — | 0.39 | — | 0.39 | — | — | 0.39 | Trace |
| Solvent | — | 150.00 | — | 150.00 | — | — | Trace | — |
| TOTAL, LB-MOLS/HR | 6.30 | 182.19 | 31.78 | 152.21 | 13.02 | 18.78 | 0.39 | 1.82 | if the proportion of $C_2+$ hydrocarbons is unusually high, the amount of methane absorbed in the solvent is proportionately less.

If only propane plus heavier hydrocarbons are desired as a liquid product, for example, up to 98% of ethane and about 1% of propane entering the process through stream 13 could leave the process via stream 12 while recovering 2% of ethane and 99% of propane from stream 13 as components of stream 95 containing 100% of the butanes and heavier hydrocarbons. These desirable recoveries can be achieved by changing the operating conditions, such that the solvent-to-fresh feed molar ratio would be significantly lowered to about 0.95 and the pressure in the medium pressure tank would be around 250 psia, the low pressure tank would operate at about 150 psia, while the demethanizer would operate as a de-ethanizer at about 275 psia.

Similarly, by changing the solvent flow rate to the extractor, changing the pressures in the subsequent flashing stages, and adjusting the pressure and temperature in the demethanizing unit, propane or butanes could be rejected to any selected degree in order to produce $C_4+$ or $C_5+$ liquid products.

EXAMPLE II

This example typifies the flexibility of the invention process, as illustrated in FIG. 2 and using the inlet gas composition given in Example I, for responding to market conditions and thereby enhancing the profitability of natural gas liquids extraction according to the procedure outlined in Example I. The basis is one million cubic feet per day (MMCFD) of sweet or pre-sweetened inlet natural gas in stream 13. The assumed price for this gas is $3.50 per million British thermal units (MMBtu). Properties and values of components of the liquid product are given in Table III.

The purchase price for the liquid product portion of the inlet natural gas is calculated as follows according to the total heat content of its components:

$$16,214.9 \frac{\text{MBtu}}{\text{hr}} \times \frac{\$3.50}{\text{MMBtu}} = \$56.75/\text{hr}$$

Gross profits are calculated as follows, using the totalled prices shown on a liquid volume basis for the individual components of the liquid product in stream 95:

$$\$81.63/\text{hr} - \$56.75/\text{hr} = \$24.88/\text{hr}$$

However, if the market price for ethane drops to 18¢/gallon, for example, while the prices for all other components remain unchanged, the market value of ethane and the revised market value of the liquid product become:

$0.18/\text{gal} \times 102.15 \text{ gal/hr} = \$18.39/\text{hr}$ for ethane
$30.65/\text{hr} - \$18.39/\text{hr} = \$12.26/\text{hr}$ less for ethane
$81.63/\text{hr} - \$12.26/\text{hr} = \$69.37/\text{hr}$ as the revised market value for the liquid product.

The revised gross profits are:

$$\$69.37/\text{hr} - \$56.75/\text{hr} = \$12.62/\text{hr}$$

TABLE III

Calculations of Quantities and Values for Components of Liquid Product Stream 95 Having a Specific Composition and Properties

| Liquid Prod. Components of Stream 95 | Properties of Components in Stream 95 | | Properties of Components in Stream 95 on Hourly Flow Basis | | | Values of Components in Stream 95 | |
|---|---|---|---|---|---|---|---|
| | Volume Gal/lb-mol | Heat Content M Btu/lb-mol | Molar lb Mols/hr | Volume Gal/hr | Heat Content M Btu/hr | Volume Basis ¢/gal | Hourly Basis $/hr |
| Methane | 6.417 | 383.18 | 0.22 | 1.41 | 84.3 | — | — |
| Ethane | 10.124 | 671.21 | 10.09 | 102.15 | 6772.5 | 30 | 30.65 |
| Propane | 10.422 | 955.27 | 5.30 | 55.24 | 5062.9 | 45 | 24.86 |
| Iso-Butane | 12.382 | 1234.39 | 0.55 | 6.81 | 678.9 | 64 | 4.36 |
| N—Butane | 11.932 | 1237.94 | 1.59 | 18.97 | 1968.3 | 62 | 11.76 |
| Iso-Pentane | 13.859 | 1517.86 | 0.33 | 4.57 | 500.9 | 68 | 3.11 |
| N—Pentane | 13.712 | 1521.25 | 0.41 | 5.62 | 623.7 | 68 | 3.82 |

TABLE III-continued

Calculations of Quantities and Values for Components of Liquid
Product Stream 95 Having a Specific Composition and Properties

| Liquid Prod. Components of Stream 95 | Properties of Components in Stream 95 | | Properties of Components in Stream 95 on Hourly Flow Basis | | | Values of Components in Stream 95 | |
|---|---|---|---|---|---|---|---|
| | Volume Gal/lb-mol | Heat Content M Btu/lb-mol | Molar lb Mols/hr | Volume Gal/hr | Heat Content M Btu/hr | Volume Basis ¢/gal | Hourly Basis $/hr |
| Hexane Plus | 15.569 | 1804.93 | 0.29 | 4.52 | 523.4 | 68 | 3.07 |
| Totals | | | 18.78 | 199.29 | 16214.9 | | 81.63 |

The fuel value of ethane can also be calculated and shows that continuing to sell ethane as a liquid product instead of as a fuel (i.e., with the residue natural gas) causes a loss:

$$6.7725 \frac{\text{MMBtu}}{\text{hr}} \times \frac{\$3.50}{\text{MMBtu}} = \$23.70/\text{hr}^*$$

*as compared to its liquid value of $18.39 at 18¢/gal

Since the operator does not have any control over feedstock pricing, as governed by supply and demand in the market, continuing to recover ethane under the low prices causes a loss of $12.26, as previously calculated. However, if the operator has an opportunity of selectively rejecting ethane because its price is lower than its fuel value, he is partially able to minimize the losses. That is, given the means, he can control his financial destiny to obtain at least the fuel value which corresponds, in this instance, to $23.70.

The following subtraction of the market value of ethane from its fuel value shows that nearly half of the drop in gross profits ($12.26) can be recouped by allowing the ethane to remain in the residue natural gas stream while continuing to extract the remaining components:

$$\$23.70/\text{hr} - \$18.39/\text{hr} = \$5.31/\text{hr}$$

However, rejecting ethane according to the process shown in FIG. 2 does not achieve perfect results; nevertheless, it permits the operator to minimize his loss to a substantial degree. The actual data for operation as a de-ethanizing process are shown in Table IV.

TABLE IV

Calculations of Quantities and Values for Components of Liquid
Product Stream 95 Having a Revised
Composition While Operating to Reject Ethane

| Liquid Product Components of Stream 95 | Properties of Components in Stream 95 on Hourly Flow Basis | | | Value of Components in Stream 95 | |
|---|---|---|---|---|---|
| | Molar lb-mols/hr | Volume Gal/hr | Heat Content M Btu/hr | Volume Basis ¢/gal | Hourly Basis $/hr |
| Methane | — | — | — | — | — |
| Ethane | 0.21 | 2.13 | 141.0 | 18 | 0.38 |
| Propane | 5.19 | 54.09 | 4957.9 | 45 | 24.34 |
| Iso-Butane | 0.55 | 6.81 | 678.9 | 64 | 4.36 |
| N—Butane | 1.59 | 18.97 | 1968.3 | 62 | 11.76 |
| Iso-Pentane | 0.33 | 4.57 | 500.9 | 68 | 3.11 |
| N—Pentane | 0.41 | 5.62 | 623.7 | 68 | 3.82 |
| Hexane Plus | 0.29 | 4.52 | 523.4 | 68 | 3.07 |
| Total | 8.57 | 96.71 | 9394.1 | | 50.84 |

The gas purchase cost for the revised liquid product of Table IV, in accordance with its total heat content, is:

$$9,394.1 \frac{\text{MBtu}}{\text{hr}} \times \frac{\$3.50}{\text{MMBtu}} = \$32.88/\text{hr}$$

Subtracting this cost from the sales price of the de-ethanized liquid product gives the following revised gross profit, with ethane at 18¢/gal:

$$\$50.84/\text{hr} - \$32.88/\text{hr} = \$17.96/\text{hr}$$

Subtracting the gross profits for the demethanized liquid product from the gross profit for the de-ethanized product, both being calculated for ethane at 18¢/gal, shows that switching to de-ethanizing has increased profits by $5.76/hr:

$$\$17.96/\text{hr} - \$12.62/\text{hr} = \$5.76/\text{hr}$$

Similar calculations can be made at any other ethane price and for depropanizing and for debutanizing at a range of prices.

The potential $C_2+$ recoveries, when operating the extraction plant for selectively treating sweet or sour natural gas with equal effectiveness, according to FIGS. 2, 3, 4, or 5 or according to other process embodiments, several of which can be incorporated into the plant and be available for use by opening and closing the appropriate valves and the like, can readily be entered in a computer program. Similarly, the price and composition of the inlet natural gas stream and the prices of the components of the liquid product can be incorporated into the same program along with costs of plant operation for each process step, such as compression after flashing to a specific pressure. A computer can thereby make calculations immediately after entry of any changed condition and then print instructions for the operator, so that the extraction plant can always be operated at the optimum profit levels.

Because it will be readily apparent to those skilled in the art of treating natural gas that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a process for the removal of natural gas liquids comprising hydrocarbons heavier than methane from a natural gas stream, wherein a need exists for recovering to any selected degree and at extremely high recoveries a selected hydrocarbon component and heavier hydrocarbons within the group consisting of ethane, propane, butane, and pentane without the need simultaneously to recover hydrocarbons lighter than said selected hydrocarbon component from said natural gas stream, the improvement comprising: providing the capability of selectively extracting said natural gas liquids from said natural gas stream with a physical solvent according to said selected degree of (a) ethane in amounts ranging from 2–98%, (b) propane in amounts ranging from 2–99%, (c) butane in amounts ranging from 2–100%; or (d) pentanes and higher molecular weight hydrocarbons in amounts ranging up to 100% by:

(1) contacting said natural gas stream with said physical solvent at flow rates within the range of 0.005–0.5 gallon of solvent per standard cubic foot of natural gas to produce a residue natural gas stream of pipeline specifications and a rich solvent stream containing ethane and heavier hydrocarbon components, said solvent being selective for ethane and heavier hydrocarbon components of the gas stream such that the relative volatility of methane over ethane is at least 5.0 and the hydrocarbon loading capacity, defined as solubility of ethane in solvent, is at least 0.25 standard cubic feet of ethane per gallon of solvent;

(2) selectively flashing said rich solvent stream to produce a gas fraction and said solvent; and (3) compressing, cooling, and condensing said gas fraction to obtain said natural gas liquids.

2. The process of claim 1, wherein said natural gas liquids are demethanized by heating said liquids to a selected bottoms temperature and at a selected pressure to remove an off-gas mixture from said liquids, said off-gas mixture comprising essentially all combined methane and selected amounts of ethane, propane, and butanes that are present in said liquids, and recycling said off-gas mixture to said contacting of said step (1).

3. The process of claim 1, wherein said contacting of said step (1) is at pipeline pressures and wherein said flow rate of said physical solvent is selectively adjusted in response to market conditions.

4. The process of claim 1, wherein said flashing of said rich solvent stream according to said step (2) is carried out in at least two successive stages at successive flashing pressures, the last flashing stage of said at least two stages being at substantially atmospheric pressure, to produce at least two $C_1+$ gas fractions having successively decreasing methane content and at least two liquid mixtures containing said solvent and successively decreasing methane content and to produce a specification liquid product, from at least the last of said at least two $C_1+$ gas fractions, which is selectively lower in methane content than said natural gas liquids of said step (3).

5. In the process of claim 4, the improvement which produces said specification liquid product having a composition which is selectively adjustable to substantially any selected degree in accordance with market conditions, comprising the use of at least one of the following additional operational procedures:

A. selectively varying the flashing pressures of said successive flashing stages to adjust the compositions of said successive gas fractions and said successive liquid mixtures relative to said selected components;

B. recycling at least the first of said successive flashed $C_1+$ gas fractions to said extracting to extract maximum quantities of said ethane and heavier hydrocarbons; and C. demethanizing at least the last of said successive $C_1+$ gas fractions to produce said specification liquid product comprising said selected components by:

(1) selectively varying the pressure of said demethanizing, and (2) selectively varying the bottoms temperature of said demethanizing.

6. The process of claim 5, wherein said natural gas stream is selected from the group consisting of:

A. natural gas saturated with water;
B. natural gas at less than saturation with water;
C. sour natural gas;
D. sour natural gas which is pre-sweetened in gas phase with an aqueous amine solution;
E. sweet natural gas; and
F. dry natural gas.

7. The process of claim 6, comprising the following steps:

A. extracting said water and said hydrocarbons heavier than methane by flowing countercurrently to said natural gas stream said physical solvent at said pipeline pressures and at said selected solvent flow rate sufficient to produce rich solvent containing said solvent, said water, and a $C_1+$ mixture of hydrocarbons, and to produce residue natural gas of pipeline quality;

B. returning said residue natural gas to a pipeline and flashing said rich solvent at a selected medium pressure to produce a $C_1$-rich gas fraction and a medium-pressure liquid mixture of said water, said solvent, and a $C_1+$ mixture of hydrocarbons, having a lower methane content than said $C_1+$ mixture of said step A;

C. flashing said medium-pressure liquid mixture at a selected low pressure to produce a $C_1$-rich gas fraction, having a lower methane content than said gas fraction of said step B, and a low-pressure liquid mixture of said water, said solvent, and a $C_1+$ mixture of hydrocarbons, having a lower methane content than said $C_1+$ mixture of step B;

D. flashing said low-pressure liquid mixture at a selected pressure of less than atmospheric pressure to produce a gas mixture of essentially all $C_1+$ hydrocarbons and a less than atmospheric-pressure liquid mixture of said water, said solvent, and minor amounts of $C_1+$ hydrocarbons;

E. regenerating said solvent by removing substantially all of said water and said minor amounts of $C_1+$ hydrocarbons from said less than atmospheric-pressure liquid mixture and returning the regenerated solvent to said extracting of said step A and returning said minor amounts of $C_1+$ hydrocarbons to said step D;

F. compressing and cooling said $C_1$-rich gas fractions produced in said step B and said step C and recycling said compressed and cooled gas fractions to said extracting of said step A;

G. compressing, cooling, and condensing said gas mixture from said step D to produce a hydrocarbon mixture;

H. demethanizing said hydrocarbon mixture by heating said hydrocarbon mixture to a selected bottoms temperature and at a selected pressure to remove an off-gas mixture from said hydrocarbon mixture, said off-gas mixture comprising essentially all of said methane and selected amounts of ethane, propane, and butanes that are present in said hydrocarbon mixture, and to produce said specification liquid product; and I. recycling said off-gas mixture to said extracting of said step A.

8. The process of claim 7, wherein said residue natural gas contains less than 7 pounds of water vapor per million standard cubic feet as said selected degree.

9. The process of claim 8, wherein said physical solvent is selected from the group consisting of dialkyl ethers of polyalkylene glycol, N-methyl pyrrollidone, dimethyl formamide, propylene carbonate, sulfolane, and glycol triacetate.

10. The process of claim 9, wherein said solvent is selected from the group consisting of dimethyl ether of polyethylene glycol, dimethyl ether of polypropylene glycol, dimethyl ether of tetramethylene glycol, and mixtures thereof.

11. The process of claim 10, wherein said solvent is a dimethyl ether of polyethylene glycol containing 3-10 ethylene units and having a molecular weight of 146 to 476.

12. The process of claim 8, wherein said regenerating is done by distillation.

13. The process of claim 12, wherein said regenerating is done by supplying heat to a reboiler to produce an overhead vaporous stream which is cooled, settled, pumped, and returned to said regenerating after disposing of excess waste water therefrom.

14. The process of claim 8, wherein said selected flashing pressures of said successive flashing stages varies between 1300 psia and 2 psia.

15. The process of claim 14, wherein said demethanizing pressure varies between 50 psia and 450 psia to reject said selected components of said liquid product.

16. The process of claim 15, wherein said bottoms temperature of said demethanizing is varied between 0° F. and 300° F.

17. The process of claim 16, wherein said process is operated to remove $C_2+$ hydrocarbon liquids from said inlet natural gas stream and to reject the methane therein as said selected degree.

18. The process of claim 17, wherein said liquid product of said demethanizing comprises up to 98% of the ethane content in said inlet natural gas stream and less than 2% of the methane content therein as said selected degree.

19. The process of claim 16, wherein said process is operated to recover $C_3+$ hydrocarbon liquids from said natural gas stream and to reject the ethane therein as said selected degree, said demethanizing being operated additionally as a de-ethanizing step.

20. The process of claim 19, wherein said liquid product of said de-ethanizing comprises up to 99% of the propane content in said natural gas stream and less than 2% of the ethane content therein as said selected degree.

21. The process of claim 16, wherein said process is operated to recover $C_4+$ hydrocarbon liquids and to reject ethane and propane therein as said selected degree, said demethanizing being additionally operated as a depropanizing step.

22. The process of claim 21, wherein said liquid product of said depropanizing comprises approximately 100% of the butanes and all heavier hydrocarbons in said natural gas stream and less than 2% of ethane and propane therein as said selected degree.

23. The process of claim 16, wherein said process is operated to recover $C_5+$ hydrocarbon liquids from said natural gas stream and to reject the ethane, propane, and butane therein as said selected degree, said demethanizing being additionally operated as a debutanizing step.

24. The process of claim 23, wherein said liquid product of said debutanizing comprises approximately 100% of the pentanes and all heavier hydrocarbons in said natural gas stream and less than 2% of ethane, propane, and butanes as said selected degree.

25. The process of claim 6, comprising the following steps:

A. extracting said water and said hydrocarbons heavier than methane by flowing countercurrently to said natural gas stream said physical solvent at said pipeline pressures and at a selected flow rate sufficient to produce rich solvent containing said solvent, said water, and a $C_1+$ mixture of hydrocarbons, and to produce said residue natural gas of pipeline quality;

B. returning said residue natural gas to a pipeline and flashing said rich solvent at a selected medium pressure to produce a $C_1$-rich gas fraction and a medium-pressure liquid mixture of said water, said solvent, and a $C_1+$ mixture of hydrocarbons having a lower methane content than said $C_1+$ mixture of said step A;

C. flashing said medium-pressure liquid mixture at a selected low pressure to produce a $C_1$-rich gas fraction having a lower methane content than said gas fraction of said step B and a low-pressure liquid mixture of said water, said solvent, and a $C_1+$ mixture of hydrocarbons having a lower methane content than said $C_1+$ mixture of said step B;

D. flashing said low-pressure liquid mixture at a selected pressure of approximately atmospheric pressure to produce a gas mixture of essentially all $C_1+$ hydrocarbons, and an atmospheric-pressure liquid mixture of said water, said solvent, and minor amounts of $C_1+$ hydrocarbons;

E. flashing said atmospheric-pressure liquid mixture at a selected pressure of less than atmospheric pressure to produce a gas mixture of most of said minor amounts of $C_1+$ hydrocarbons and a less than atmospheric-pressure liquid mixture of said water, said solvent, and trace amounts of $C_1+$ hydrocarbons;

F. regenerating said solvent by removing said water and said trace amounts of $C_1+$ hydrocarbons from said less than atmospheric-pressure liquid mixture and returning the regenerated solvent to said extracting of said step A and returning said trace amounts of $C_1+$ hydrocarbons to said step E;

G. compressing and cooling said $C_1$-rich gas fractions produced in said step B and said step C and recycling said compressed and cooled gas fractions to said extracting of said step A;

H. compressing, cooling, and condensing said gas mixture from said step D and said step E to produce a hydrocarbon mixture;

I. demethanizing said hydrocarbon mixture by heating said hydrocarbon mixture to a selected bottoms temperature and at a selected pressure to remove an off-gas mixture from said hydrocarbon mixture, said off-gas mixture comprising essentially all of said methane and selected amounts of ethane, propane, and butanes that are present in said hydrocarbon mixture, and to produce said specification liquid product; and J. recycling said off-gas mixture to said extracting of said step A.

26. The process of claim 25, wherein said approximately atmospheric pressure is up to about 25 psia and said less than atmospheric pressure is at least 2 psia, depending upon the content of $C_5+$ hydrocarbons in said inlet natural gas stream.

27. The process of claim 6, comprising the following steps:
  A. extracting said water and said hydrocarbons heavier than methane by flowing countercurrently to said natural gas stream said physical solvent at said pipeline pressures and at a selected solvent flow rate sufficient to produce rich solvent containing said solvent, said water, and a $C_1+$ mixture of hydrocarbons, and to produce residue natural gas of pipeline quality;
  B. returning said residue natural gas to a pipeline and flashing said rich solvent at a selected medium pressure to produce a $C_1$-rich gas fraction and a medium-pressure liquid mixture of said water, said solvent, and a $C_1+$ mixture of hydrocarbons having a lower methane content than said $C_1+$ mixture of said step A;
  C. flashing said medium-pressure liquid mixture at a selected low pressure to produce a $C_1$-rich gas fraction having a lower methane content than said gas fraction of said step B and a low-pressure liquid mixture of said water, said solvent, and a $C_1+$ mixture of hydrocarbons having a lower methane content than said $C_1+$ mixture of said step B;
  D. flashing said low-pressure liquid mixture at a selected pressure of approximately atmospheric pressure to produce a gas mixture of essentially all $C_1+$ hydrocarbons, and an atmospheric-pressure liquid mixture of said water, said solvent, and minor amounts of $C_1+$ hydrocarbons;
  E. flashing said atmospheric-pressure liquid mixture at a selected pressure of less than atmospheric pressure to produce a gas mixture of most of said minor amounts of $C_1+$ hydrocarbons and a less than atmospheric-pressure liquid mixture of said water, said solvent, and trace amounts of $C_1+$ hydrocarbons;
  F. regenerating said solvent by removing said water and said trace amounts of $C_1+$ hydrocarbons from said less than atmospheric-pressure liquid mixture and returning the regenerated solvent to said extracting of said step A and returning said trace amounts of $C_1+$ hydrocarbons to said step E;
  G. compressing, cooling, and condensing said gas mixtures from said step B, said step C, said step D, and said step E to produce a hydrocarbon mixture;
  H. demethanizing said hydrocarbon mixture by heating said hydrocarbon mixture from said step G to a selected bottoms temperature and at a selected pressure to remove an off-gas mixture from said hydrocarbon mixture, said off-gas mixture comprising essentially all of said methane and selected amounts of ethane, propane, and butanes that are present in said hydrocarbon mixture, and to produce said specification liquid product; and
  I. recycling said off-gas mixture to said extracting of said step A.

28. The process of claim 27, wherein said approximately atmospheric pressure is up to about 25 psia and said less than atmospheric pressure is at least 2 psia, depending upon the content of $C_5+$ hydrocarbons in said inlet natural gas stream.

29. The process of claim 6, comprising the following steps:
  A. extracting said water and said hydrocarbons heavier than methane by flowing countercurrently to said natural gas stream said physical solvent at said pipeline pressures and at a selected solvent flow rate sufficient to produce rich solvent containing said solvent, said water, and a $C_1+$ mixture of hydrocarbons, and to produce residue natural gas of pipeline quality;
  B. returning said residue natural gas to a pipeline and flashing said rich solvent at a selected medium pressure to produce a $C_1$-rich gas fraction and a medium-pressure liquid mixture of said water, said solvent, and a $C_1+$ mixture of hydrocarbons having a lower methane content than said $C_1+$ mixture of said step A;
  C. flashing said medium-pressure liquid mixture at a selected low pressure to produce a $C_1$-rich gas fraction having a lower methane content than said gas fraction of said step B and a low-pressure liquid mixture of said water, said solvent, and a $C_1+$ mixture of hydrocarbons having a lower methane content than said $C_1+$ mixture of said step B;
  D. flashing said low-pressure liquid mixture at a selected pressure of approximately atmospheric pressure to produce a gas mixture of essentially all $C_1+$ hydrocarbons and an atmospheric-pressure liquid mixture of said water, said solvent, and minor amounts of $C_1+$ hydrocarbons;
  E. regenerating said solvent by removing said water and said minor amounts of $C_1+$ hydrocarbons from said approximately atmospheric-pressure liquid mixture and returning the regenerated solvent to said extracting of said step A and returning said minor amounts of $C_1+$ hydrocarbons to said step D;
  F. compressing and cooling said $C_1$-rich gas fractions produced in said step B and said step C and recycling said compressed and cooled gas fractions to said extracting of said step A; and
  G. compressing, cooling, and condensing said gas mixture from said step D to produce said specification liquid product.

30. The process of claim 29, wherein said natural gas stream is rich in $C_5+$ hydrocarbons and wherein said process further comprises flashing said atmospheric-pressure liquid mixture at a selected pressure of substantially less than atmospheric pressure to produce a $C_1+$-rich gas mixture and a less-than atmospheric pressure liquid mixture of said water, said solvent, and trace amounts of $C_1+$ hydrocarbons which is sent to said regenerating of said step E of claim 29, said $C_1+$-rich gas mixture being sent to said step G of claim 29 in addition to said gas mixture from said step D of claim 29.

31. The process of claim 29, wherein said gas mixture of said step D of claim 29 is compressed, cooled, and condensed for demethanizing by heating said mixture to a selected bottoms temperature and at a selected pressure to remove an off-gas mixture from said mixture, said off-gas mixture comprising essentially all of said methane and selected amounts of ethane, propane, and butanes that are present in said mixture, and recycling said off-gas mixture to said extracting of said step A of claim 29.

32. The process of claim 6, wherein said extracting is conducted at 20°–120° F.

33. The process of claim 32, wherein said extracting is conducted at 70°–80° F.

34. The process of claim 6, wherein said extracting is conducted at 300–1300 psig.

35. The process of claim 6, comprising removing water, acid gases, and hydrocarbons heavier than methane to substantially any selected degree from a sour natural gas stream, containing acid gases and water, by the following steps:
- A. extracting said water, said acid gases, and said hydrocarbons heavier than methane by flowing countercurrently to said natural gas stream said physical solvent at pipeline pressures and at a selected solvent flow rate sufficient to produce rich solvent containing said solvent, said water, said acid gases, and a $C_1+$ mixture of hydrocarbons, and to produce said residue natural gas of pipeline quality;
- B. returning said residue natural gas to a pipeline and flashing said rich solvent at a selected medium pressure to produce a $C_1$-rich gas fraction and a medium pressure liquid mixture of said water, said solvent, said acid gases, and a $C_1+$ mixture of hydrocarbons having a lower methane content than said $C_1+$ mixture of said step A;
- C. flashing said medium-pressure liquid mixture at selected low pressure to produce a $C_1$-rich gas fraction having a lower methane content than said gas fraction of said step B and a low-pressure liquid mixture of said water, said solvent, said acid gases, and a $C_1+$ mixture of hydrocarbons having a lower methane content than said $C_1+$ mixture of said step B;
- D. flashing said low-pressure liquid mixture at a selected pressure of approximately atmospheric pressure to produce a gas mixture of essentially all $C_1+$ hydrocarbons, a portion of said acid gases, and an atmospheric-pressure liquid mixture of said water, said solvent, minor amounts of $C_1+$ hydrocarbons and the remaining portion of said acid gases;
- E. flashing said atmospheric-pressure liquid mixture at a selected pressure of less than atmospheric pressure to produce a gas mixture of most of said minor amounts of $C_1+$ hydrocarbons and a major portion of said remaining portion of acid gases and a less-than-atmospheric-pressure liquid mixture of said water, said solvent, trace amounts of $C_1+$ hydrocarbons and the minor portion of said remaining portion of acid gases;
- F. regenerating said solvent by removing said water, said trace amounts of $C_1+$ hydrocarbons, and said minor portion of acid gases from said less than atmospheric-pressure liquid mixture and returning the regenerated solvent to said extracting of said step A and returning said trace amounts of $C_1+$ hydrocarbons and said minor portion of acid gases to said step E;
- G. compressing and cooling said $C_1$-rich gas fractions produced in said step B and said step C and recycling said compressed and cooled gas fraction to said extracting of said step A;
- H. compressing, cooling and condensing said gas mixtures from said step D and said step E to produce a sour hydrocarbon mixture;
- I. demethanizing said sour hydrocarbon mixture by heating said sour hydrocarbon mixture from said step H to a selected bottoms temperature and at a selected pressure to remove an off-gas mixture from said sour hydrocarbon mixture, said off-gas mixture comprising essentially all of said methane and selected amounts of ethane, propane, butanes and acid gases that are present in said sour hydrocarbon mixture, and to produce a sour liquid product containing said acid gases;
- J. recycling said off-gas mixture of said step I to said extracting of said step A; and
- K. treating said sour liquid product of said step I with an amine stream to produce said specification liquid product and an acid gas stream.

36. The process of claim 1, wherein said natural gas contains water and said solvent of step (2) is regenerated by removing said water and minor amounts of $C_1+$ hydrocarbons from said solvent of said step (2) and returning the regenerated solvent to said contacting of said step (1) and returning said minor amounts of $C_1+$ hydrocarbons to said step (3).

* * * * *

UNITED STATES PATENT AND TRADEMARK OFFICE
CERTIFICATE OF CORRECTION

PATENT NO. : 4,511,381
DATED : April 16, 1985
INVENTOR(S) : Yuv R. Mehra

It is certified that error appears in the above—identified patent and that said Letters Patent is hereby corrected as shown below:

Cover page, first column, line 14, change "4,421,534" to --4,421,535--.

Column 1, line 7, change "4,421,534" to --4,421,535--.

Column 17, line 22, change "ISO-Butane" to --ISO-Pentane--.

In the claims:

Claim 8, line 1, change "claim 7," to --claims 7, 25, 26, 27, 28, 29, 30, 31, and 35,--.

Claim 25, line 6, insert --solvent-- after "selected".

Claim 35, column 30, line 16, change "fraction" to --fractions--.

Signed and Sealed this

Twenty-fourth Day of September 1985

[SEAL]

Attest:

Attesting Officer

DONALD J. QUIGG

Commissioner of Patents and Trademarks—Designate